US012752034B2

(12) United States Patent
Armijo et al.

(10) Patent No.: US 12,752,034 B2
(45) Date of Patent: Oct. 6, 2026

(54) CABLE RACK SYSTEMS AND RELATED METHODS

(71) Applicant: PURO Lighting, LLC, Lakewood, CO (US)

(72) Inventors: Adrian Armijo, Arvada, CO (US); Alexandre Wamain, Denver, CO (US); Jesse Sfetsas, Lakewood, CO (US)

(73) Assignee: Airocide Systems, LLC, Neptune Beach, FL (US)

( * ) Notice: Subject to any disclaimer, the term of this patent is extended or adjusted under 35 U.S.C. 154(b) by 450 days.

(21) Appl. No.: 18/126,073

(22) Filed: Mar. 24, 2023

(65) Prior Publication Data

US 2023/0321309 A1 Oct. 12, 2023

Related U.S. Application Data

(60) Provisional application No. 63/323,414, filed on Mar. 24, 2022.

(51) Int. Cl.
*A61L 9/20* (2006.01)
*A61L 2/10* (2026.01)
*A61L 2/24* (2006.01)

(52) U.S. Cl.
CPC .................................... *A61L 9/20* (2013.01); *A61L 2/10* (2013.01); *A61L 2/24* (2013.01); *A61L 2202/11* (2013.01); *A61L 2209/12* (2013.01); *A61L 2209/15* (2013.01)

(58) Field of Classification Search
CPC ..... A61L 9/20; A61L 2/10; A61L 2/24; A61L 2202/11; A61L 2209/12; A61L 2209/15
See application file for complete search history.

(56) References Cited

U.S. PATENT DOCUMENTS

| | | | | |
|---|---|---|---|---|
| 7,229,195 | B2 | 6/2007 | Witham et al. | |
| 10,105,463 | B2 | 10/2018 | Kim et al. | |
| 10,179,016 | B1 * | 1/2019 | Bryant | A61B 17/683 |
| 11,460,173 | B1 * | 10/2022 | Brooks | H05K 1/0266 |
| 2015/0274549 | A1 | 10/2015 | Huang et al. | |
| 2018/0228676 | A1 * | 8/2018 | Merdek | H05B 47/11 |

FOREIGN PATENT DOCUMENTS

| | | | | |
|---|---|---|---|---|
| CN | 2636135 | Y | 8/2004 | |
| CN | 2683122 | Y | 3/2005 | |
| CN | 2722913 | Y | 9/2005 | |
| CN | 107998412 | A | 5/2018 | |
| DE | 202020107000 | U1 | 3/2021 | |
| KR | 20060039360 | A | 5/2006 | |
| WO | WO-2021231907 | A1 * | 11/2021 | B64D 13/00 |

* cited by examiner

*Primary Examiner* — Andrew Smyth
(74) *Attorney, Agent, or Firm* — Assouline & Berlowe, P.A.; David R. O'Steen

(57) ABSTRACT

A cable rack system apparatus for assisting the user with installation, disinfection, and mounting to a surface includes one or more cables, one or more ultraviolet ("UV") emitters, one or more clips, and two or more surface mounts. The one or more UV emitters are coupled to the one or more cables with one or more clips. Other embodiments are described herein.

19 Claims, 22 Drawing Sheets

FIG. 8
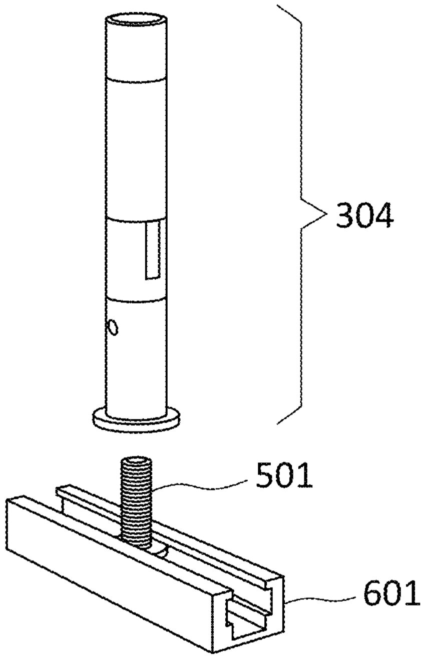
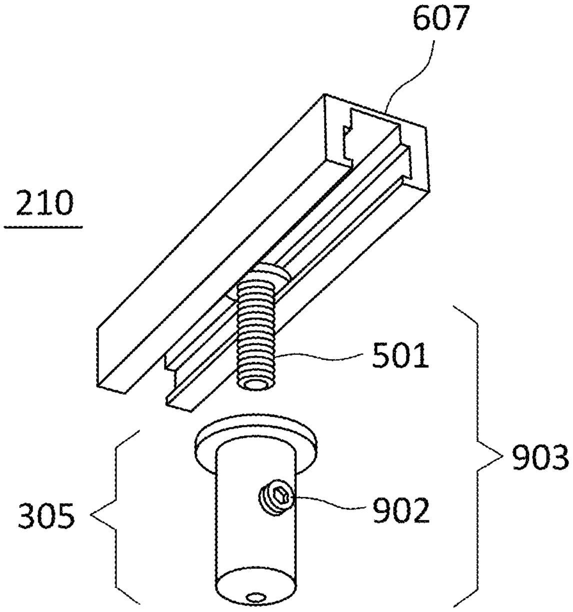
FIG. 9

CABLE RACK SYSTEMS AND RELATED METHODS

CROSS-REFERENCE TO RELATED APPLICATION

This application claims the benefit of U.S. Provisional Application No. 63/323,414, filed Mar. 24, 2022. U.S. Provisional Application No. 63/323,414 is incorporated herein by reference in its entirety.

TECHNICAL FIELD

The present disclosure generally relates to ultraviolet ("UV") emitter rack systems using one or more cables.

BACKGROUND

This section provides background information related to the present disclosure which is not necessarily prior art. The section headings used herein are solely for organization purposes and are not to be construed as limiting the subject matter described in any way.

Rack systems are often used to arrange or store objects within a space. Users or distributors of rack systems may struggle to store component parts of large rack systems prior to assembly and installation. Cable rack systems can include multiple component parts, complicating the installation and assembly process. Prior racking systems utilized one or more large extrusions and rigid components that would not function if any component was misaligned or improperly installed. A misalignment of one such component could require the installer to disassemble the racking system and start over with the assembly. The functionality of prior rack systems was impaired by their lack of flexibility and inability to accommodate different component sizes or preferred orientations. Additionally, prior racking systems that do not utilize cables have greater surface area creating a greater disruption to airflow around the cable rack system.

SUMMARY OF THE DISCLOSURE

This section provides a general summary of the disclosure, and is not a comprehensive disclosure of its full scope or all of its features.

Among the various aspects of the present disclosure is a cable rack system as substantially shown and described.

Embodiments of the present disclosure provide a cable rack system for holding ultraviolet ("UV") emitters. This cable racking system can comprise one or more cables, one or more clips, one or more UV emitters, and two or more surface mounts. One or more clips can be coupled to the one or more cables to receive one or more UV emitters of the cable racking system. Two or more surface mounts can be used to secure the cables, clips, and UV emitters of the cable racking system to the use environment. The surface mount can be coupled to surfaces including a ceiling and/or floor surface, a top and/or bottom mounting surface (e.g., a track or plate), one or more walls and/or sloped surfaces, and/or a frame with one or more wheels. The use environment can include an air handling system, a vertically oriented object, a horizontally oriented object, gas, liquid, and/or solid components.

Additional embodiments include a method of providing a cable rack system. The method can include providing one or more cables, providing one or more UV emitters, providing two or more surface mounts, providing one or more clips, and providing a sliding frame. The sliding frame can have one or more wheels. In some embodiments, the frame may have a surface finish that allows for sliding across a surface without the need for wheels. The two or more surface mounts can be configured to couple the one or more cables to two or more surfaces. The one or more clips can be provided to couple the one or more cables to the one or more UV emitters. A frame with one or more wheels can be provided to couple at least one of the one or more surface mounts to the frame to secure the cable rack system. Additional embodiments include a method of installing a cable rack system. The method can include coupling one or more UV emitters to one or more cables using one or more clips, coupling one or more cables to two or more surfaces using two or more surface mounts, and coupling at least one of the two or more surface mounts to a frame with one or more wheels.

The cable is for securing one or more UV emitters to two or more surfaces. The cable rack system can use one or more cables. In one embodiment, two cables can be oriented parallel to each other to secure one or more UV emitters at various locations between the cables and between the bottom or floor surface and the top or ceiling surface of the use environment. In another embodiment, several smaller pieces of cable can be used to secure one or more UV emitters at various locations between the bottom surface and the top surface. The same or different cable type can be used. In another embodiment, one or more cables can run from one side surface or wall to another side surface or wall, either from left to right or right to left. In some embodiments, one or more cables can be oriented approximately parallel to the one or more UV emitters. In some embodiments, the one or more cables can be oriented approximately perpendicular to the one or more UV emitters coupled to the one or more cables.

The UV emitter can be located between one or more clips coupled to one or more cables. If a single cable, or one clip per UV emitter is used, the center portion of the UV emitter can be coupled to the clip so that the UV emitter is balanced on the clip. If two clips are used per UV emitter, one clip can be coupled to the right side of the UV emitter and one clip can be coupled to the left side of the UV emitter. The UV emitters of the cable rack system can emit the same or different colors and/or wavelengths. The location of the one or more clips can be adjusted along the one or more cables to receive UV emitters of different widths, or allow for different spacing between the one or more UV emitters. The one or more clips can have an adjustable mechanism that allows for the movement of the one or more clips along the cable. The UV emitter can be an LED board with one or more LED lights.

The surface mount is for mounting the cable rack system to a fixed or moveable surface in the use environment. In one embodiment, one or more universal surface mounts (e.g. FIGS. 1, 16, 17, 18, 19) can be used to secure the cable rack system to a bottom, floor, or right surface and one or more surface mounts can be used to secure the cable rack system to a top, ceiling, or left surface. In another embodiment, a track surface mount (e.g. FIGS. 2-10, 20) can be used to secure one or more surface mounts of the cable rack system to a bottom, floor, or right track surface and one or more surface mounts of the cable rack system to a top, ceiling, or left track surface. A surface mount can be adjusted to couple to one or more locations along the track surface. The surface mount can be coupled to the track surface by a hexagonal head nut and bolt, a rectangular head nut and bolt, or other fastener. In another embodiment, one or more jointed surface mounts can be used to secure the cable rack system to one or more walls or slopped surfaces. The jointed surface mount can extend approximately perpendicular to the one or more cables to couple the cable rack system to one or more surfaces approximately parallel to the cable. In yet another embodiment, a frame mount can be used to secure the cable rack system to a sliding or rolling frame.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 8. is a front, right side view of the bottom channel nut, hexagonal head channel bolt, and the bottom mount of FIG. 7;

FIG. 9 is a front, right side view of the top anchor and a top mount, according to an embodiment of the present invention;

Figure 1:
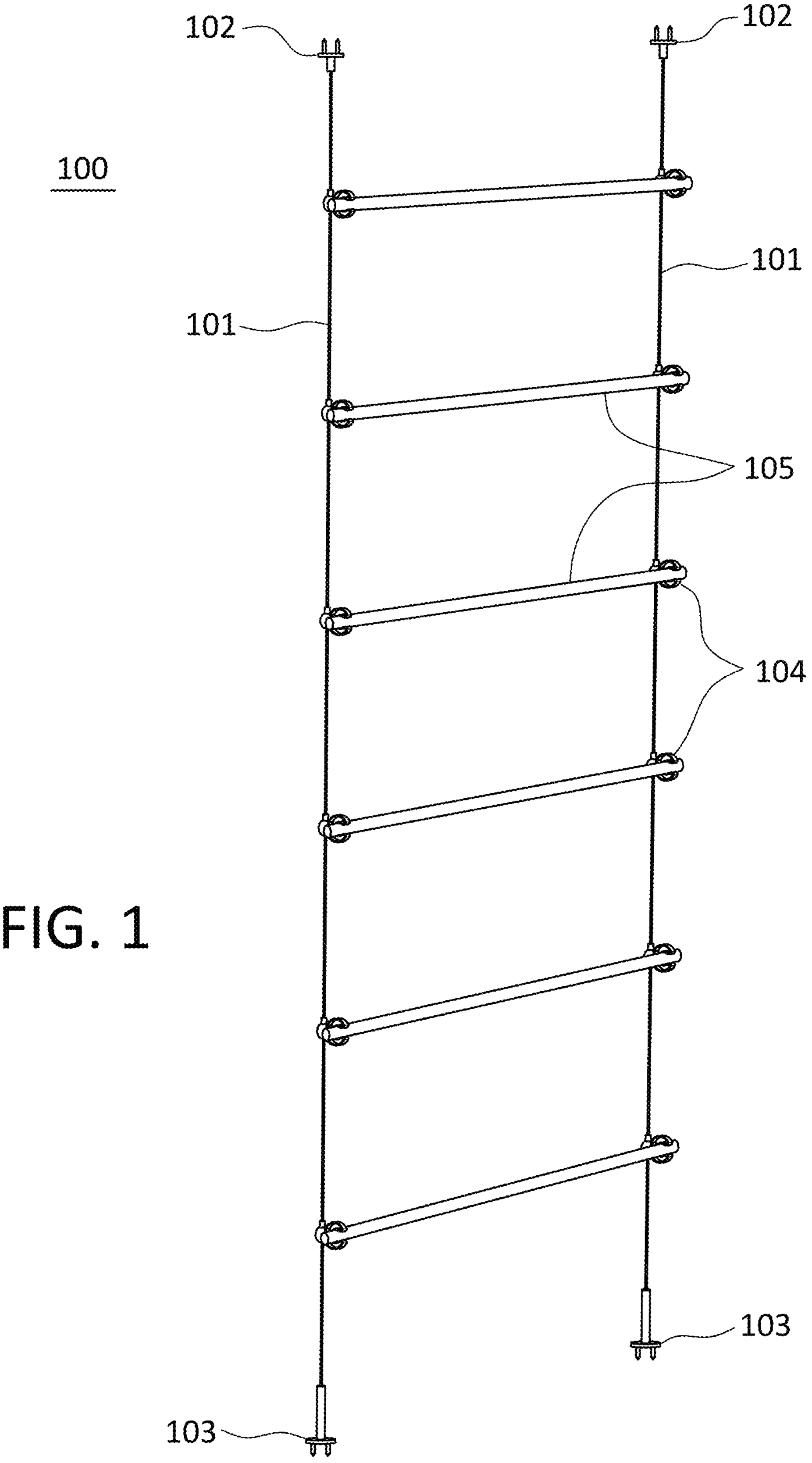
FIG. 1 is a front, left side perspective view of a cable rack apparatus, according to an embodiment of the present invention, with a top anchor and a bottom anchor.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," and the like in the description and in the claims are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, when introducing elements of the present invention or the illustrated embodiments thereof, the articles "a," "an," "the," and "said" are intended to mean that there are one or more of the elements. The terms "comprising," "including," and "having" are intended to be inclusive and mean that there may be additional elements other than the listed elements. For example, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements mechanically and/or otherwise. Coupling may be for any length of time, e.g., permanent or semi-permanent or only for an instant. The absence of the word "removably," "removable," and the like near the word "coupled," and the like does not mean that the coupling, etc. in question is or is not removable.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DETAILED DESCRIPTION OF EXAMPLES OF EMBODIMENTS

Example embodiments will now be described more fully with reference to the accompanying drawings.

Before any aspects of the disclosure are explained in detail, it will be understood that the disclosure is not limited in its application to the details of construction and the arrangement of components set forth in the following description or illustrated in the following drawings. The disclosure is capable of other aspects and of being practiced or of being carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. All numbers expressing measurements and so forth used in the specification and claims are to be understood as being modified in all instances by the term "approximately."

Turning now to the drawings, FIG. 1 displays an exemplary cable rack system 100. Cable rack system 100 is merely exemplary, and embodiments of the cable rack system are not limited to the embodiments presented herein. The cable rack system can be employed in many different embodiments or examples not specifically depicted or described herein. In many embodiments, cable rack system 100 can comprise one or more cables 101, one or more top anchors 102, one or more bottom anchors 103, one or more clip assemblies 104, and/or one or more UV emitters 105.

Generally speaking, cable 101 can comprise an approximately cylindrical strand or rod of metal. In various embodiments, cable 101 can be flexible. In some embodiments, cable 101 can comprise multiple rods or strands of metal joined together. For example, cable 101 can comprise strands joined together with a clamp or some other fastener. As another example, cable 101 can comprise multiple strands of metal braided together into a rope. As a further example, aircraft cable can be used. Cable 101 can have a number of different diameters. In some examples, cable 101 can be a 7×7 cable, which includes 7 coils each having 7 strands. As other examples, cable 101 can be a 7×19 cable, which includes 7 coils each having 19 strands. In some embodiments, cable 101 can have an approximately 1/16 inch (0.159 centimeter (cm)) diameter to an approximately 1/8 inch (0.318 cm) diameter. For example, the cable can be approximately 3/32 inch (0.238 cm) diameter.

In some embodiments, cable rack system 100 can use one cable (e.g., 101) spanning from top anchor 102 to bottom anchor 103. In other embodiments, two or more cables (e.g., 101) can span from top anchor 102 to bottom anchor 103. In various embodiments, cable 101 can be split into segments and each segment can be connected by a clip (e.g., clip assembly 104) or other suitable fastener. Cable 101 can be of a number of different lengths based upon available stock and/or standardized lengths for a particular cable. For example, cable 101 can comprise a 240 inch (609.6 cm) cable. Using a cable (e.g., 101) in cable rack system 100 can impart a number of benefits. For example, using a cable can offer increased forgiveness when installing a racking system. In some embodiments, cables can be misaligned but, due to their flexibility one or more lamps can be racked without being damaged. This can allow an installer to be less precise with installation, thereby saving time. In many embodiments, cable 101 can have an approximately 15.27 square inches (38.786 square centimeters) of cross sectional area. The reduced cross sectional area and weight can impart an improvement over prior racking systems. For example, when compared with extrusion racking systems, which can have a cross sectional area of approximately 145.27 square inches (368.986 square centimeters), a savings of approximately 130 square inches (330.2 square centimeters) (i.e. approximately 89.5%) can lead to savings on material, weight, and shipping costs in a cable rack system. Additionally, the decreased surface area can result in less disruption to flow as air, liquid, or gas passes through the cable rack system (e.g., 100).

In various embodiments, cable 101 can be coupled to one or more surface mounts. Exemplary surface mounts include top anchors (e.g. 102, 203, 903, 1910) and/or bottom anchors (e.g. 103, 204, 504, 1920). It should be understood that cable rack system 100 (and other cable racking systems describe herein) need not be limited to vertical cable installation. In many embodiments, top anchors (e.g. 102, 203, 903, 1910) and/or bottom anchors (e.g. 103, 204, 504, 1920) can be affixed to one or more side walls such that cable 101 is oriented horizontally. In these embodiments, top anchors (e.g. 102, 203, 903, 1910) and/or bottom anchors (e.g. 103, 204, 504, 1920) can be referred to as side anchors.

Figure 20:
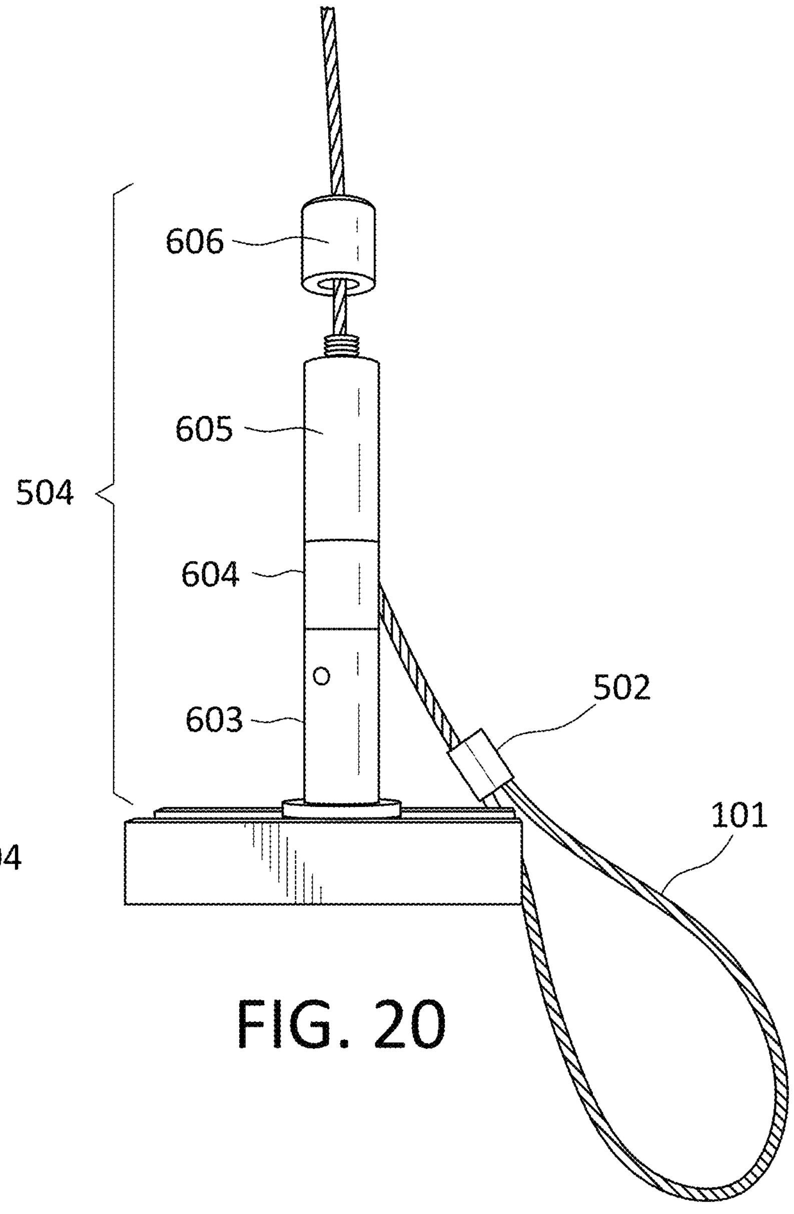
FIG. 20 is a front view of the bottom anchor and bottom mount of FIGS. 7-8.
Figure 21:
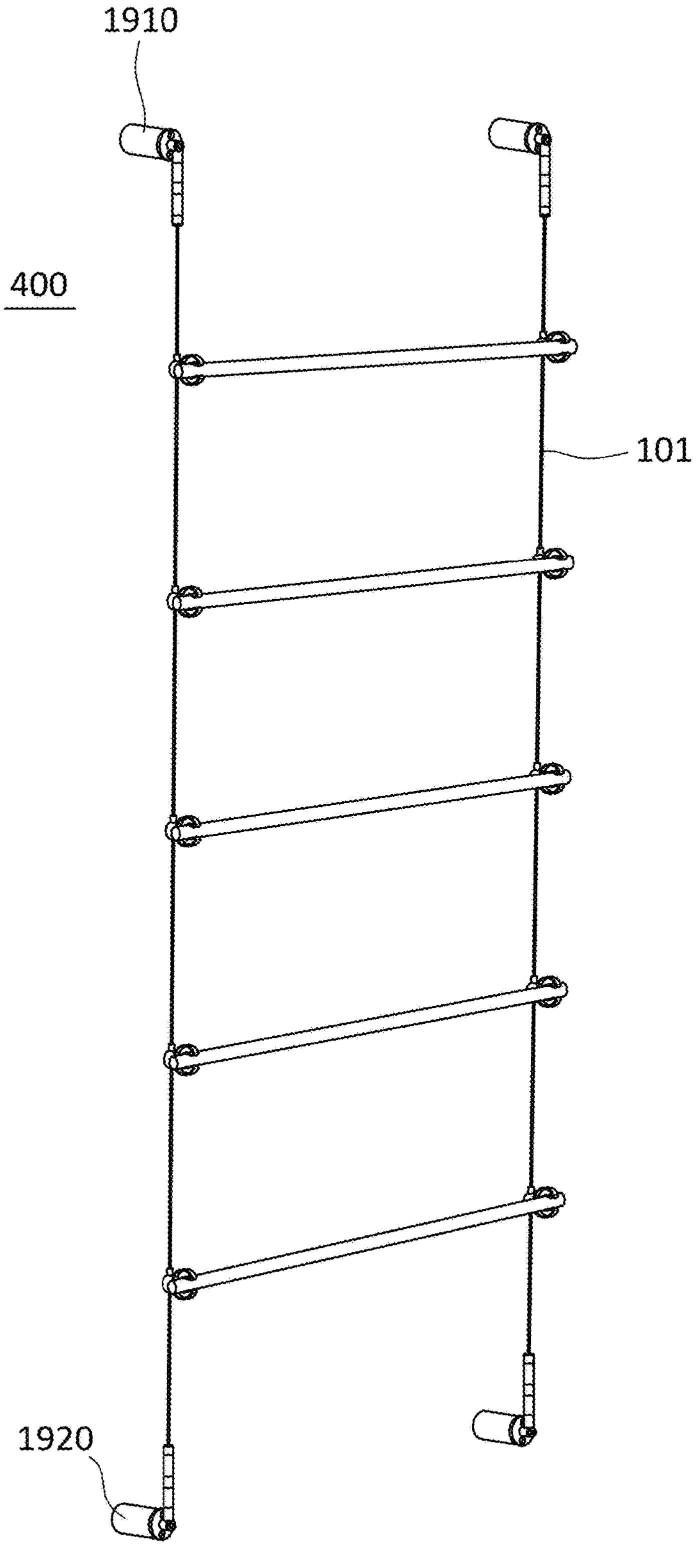
FIG. 21 is a front, left side view of a cable rack apparatus with jointed feet, according to an embodiment of the present invention.

In some embodiments, top anchors (e.g. 102, 1910) and/or bottom anchors (e.g. 103, 1920) are surface mounts that can be configured to be coupled directly to one or more surfaces (e.g., one or more walls, ceilings, floors, etc.) using one or more fasteners (e.g., nails, screws, bolts, adhesive, etc.) as shown in FIG. 1. Top anchors 102 and bottom anchors 103 of FIG. 1 are universal surface mounts. Universal surface mounts can be mounted to a variety of surface types (e.g. ceilings, floors, walls, frames, ramps, etc.). Top anchors 1910 and bottom anchors 1920 of FIG. 21 are jointed surface mounts. In many embodiments, one or more of top anchors (e.g. 102, 203, 903, 1910) and/or bottom anchors (e.g. 103, 204, 504, 1920) can be configured to adjust a tension of cable 101. For example, portions of top anchors (e.g. 102, 203, 903, 1910) and/or bottom anchors (e.g. 103, 204, 504, 1920) can expand or contract to loosen or tighten the tension of cable 101, as shown in FIG. 20. Additional details about anchors useful in a cable racking system are described below.

Figure 2:
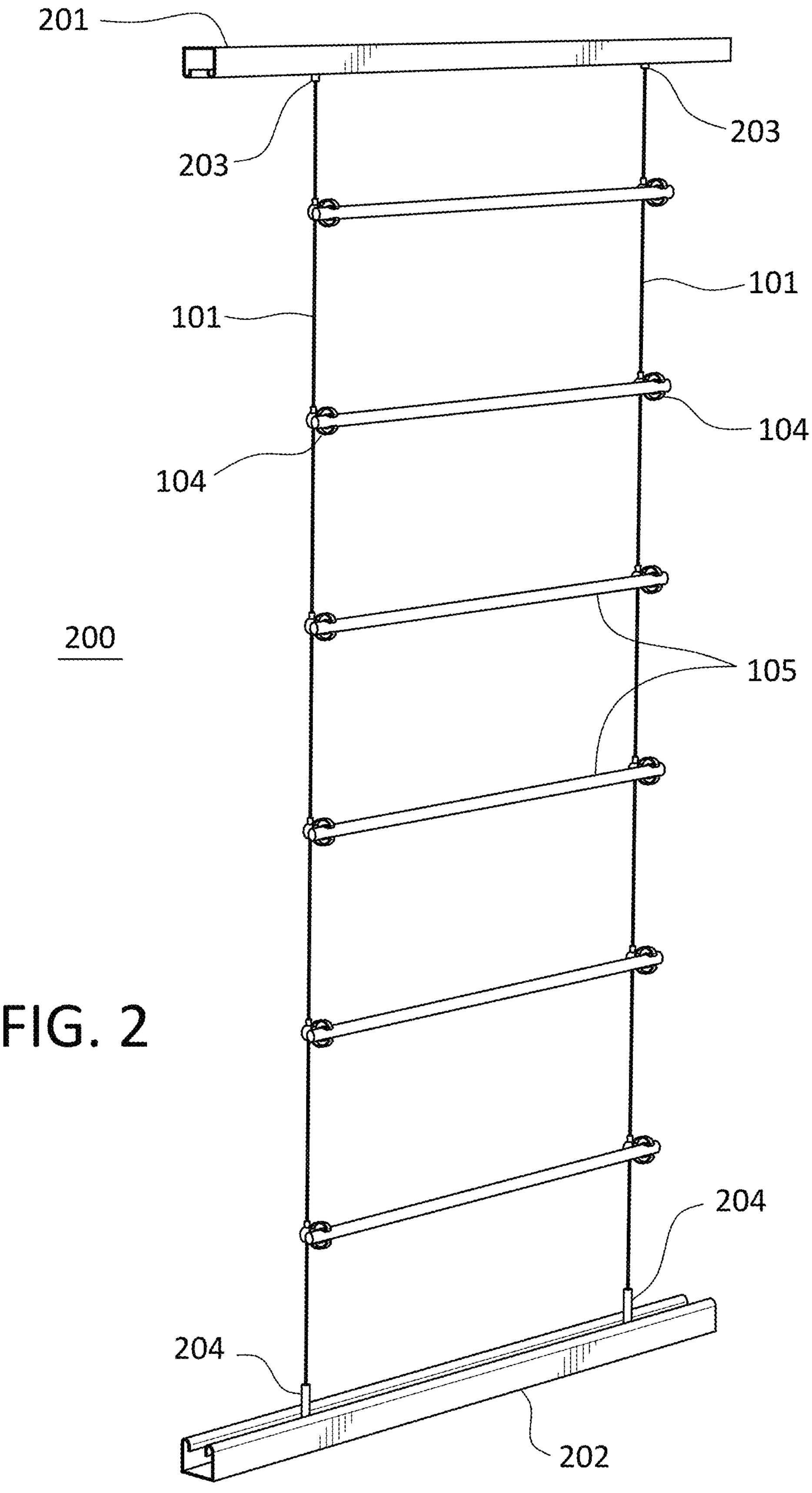
FIG. 2 is a front, left side perspective view of a cable rack apparatus, according to an embodiment of the present invention, with a top mount and a bottom mount.

Turning now to FIG. 2, an exemplary cable rack system 200 is shown. Cable rack system 200 is merely exemplary, and embodiments of the cable rack system are not limited to the embodiments presented herein. The cable rack system can be employed in many different embodiments or examples not specifically depicted or described herein. Cable rack system 200 can be similar to cable rack system 100 (FIG. 1), and various elements of cable rack system 200 can be similar or identical to various elements of cable rack system 100 (FIG. 1). In many embodiments, cable rack system 200 can comprise one or more cables 101, one or more top anchors 203, one or more bottom anchors 204, one or more clip assemblies 104, one or more UV emitters 105, one or more top mounts 201, and/or one or more bottom mounts 202. Generally speaking, one or more top mounts 201, and/or one or more bottom mounts 202 can comprise a channel configured to receive one or more top anchors 203, one or more bottom anchors 204, respectively. Top mount 201 can be installed to a ceiling surface, and bottom mount 202 can be installed to a floor surface. Top anchor 203 can be similar or identical to top anchor 102. Bottom anchor 204 can be similar or identical to bottom anchor 103. In some embodiments, top mount 201 and/or bottom mount 202 can comprise a formed and/or extruded metal channel. For example, top mount 201 and/or bottom mount 202 can comprise a formed and/or extruded metal channel or track surface (e.g., a Unistrut 8020 and/or T-track). The mount can be metal (e.g., Aluminum, Nickel, Steel, etc.), polymer, plastic, or any other suitable material. Using a channel for a top mount and/or bottom mount can allow for a number of advantages. For example, a channel allows for easy adjustment to a cable racking system. A channel can also cause one or more UV emitters 105 of a cable racking system to be in a same plane and/or parallel to that of the channel. As another example, a channel can allow bottom anchors and/or top anchors to be adjusted within the channel, thereby allowing for different sized UV emitters. A channel can provide a level surface for top anchor 203 and bottom anchor 204 in an environment where utilizing a universal or direct mounting system with top anchor 102 and bottom anchor 103 may alter the alignment of the system.

Figure 3:
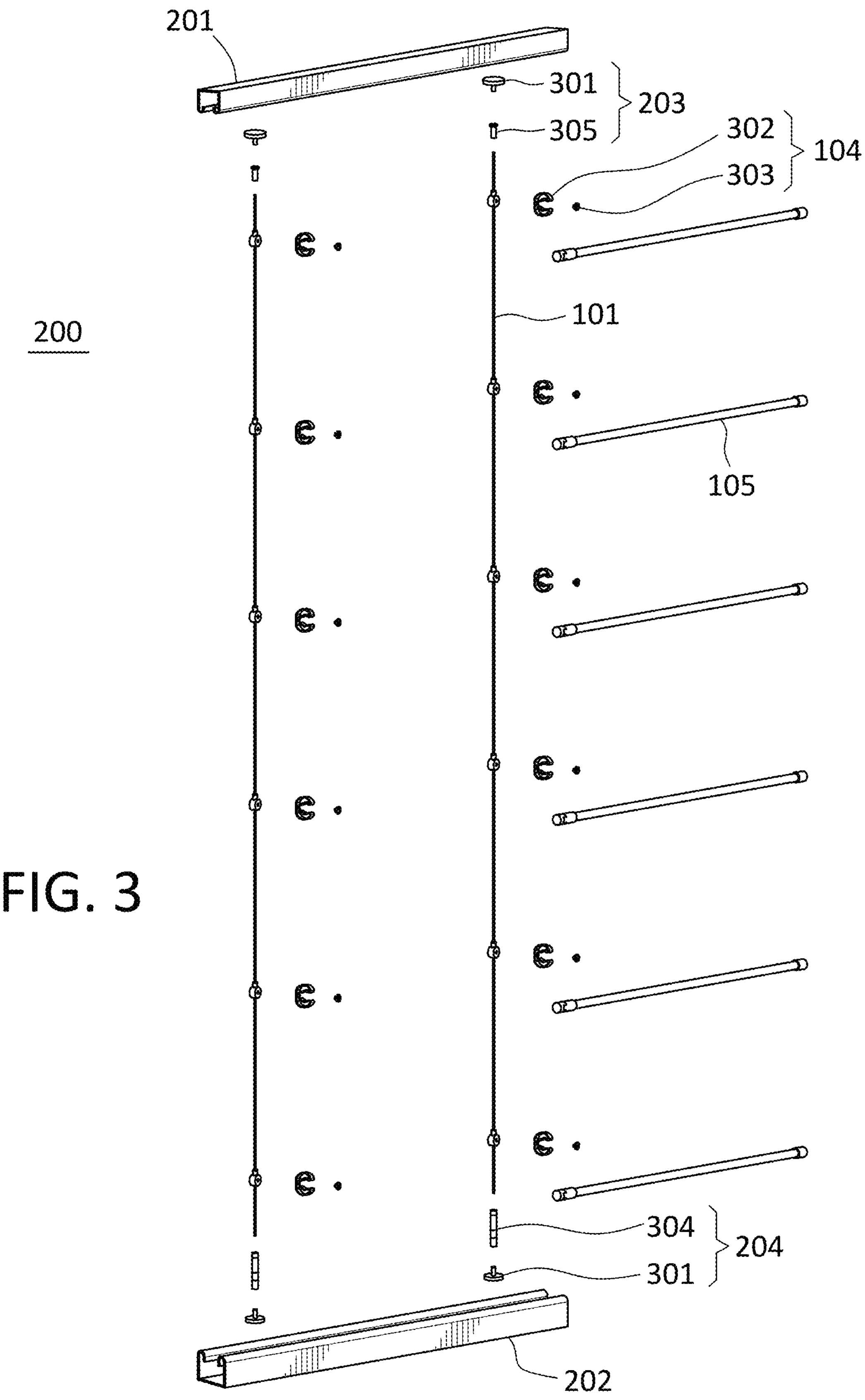
FIG. 3 is an exploded front, left side perspective view of the cable rack apparatus of FIG. 2.

Turning now to FIG. 3, an exploded view of cable rack system 200 is shown. This exploded view shows top mount 201, one or more top anchors 203, one or more cables 101, one or more UV emitters 105, one or more clip assemblies 104, one or more bottom anchors 204, and bottom mount 202. In some embodiments, bottom anchor 204 can comprise one or more of bottom channel nut 304 and/or one or more channel bolt 301. Channel bolt 301 can have a rectangular or strut head as shown in FIG. 3. In some embodiments, top anchor 203 can comprise one or more of top channel nut 305 and/or one or more channel bolt 301. In some embodiments, clip assembly 104 can comprise one or more cable gripper 1220 (as shown in FIGS. 12-15 and described below), one or more cable gripper cap 1210 (as shown in FIGS. 12-15 and described below), one or more UV emitter clip 302, and/or one or more fastener 303. Additional details about the use of clips in a cable racking system are described below.

The top and bottom track surfaces of cable rack system 200 (e.g. 201, 202) as shown in FIGS. 2-3 are configured to receive channel bolt 301 which has a rectangular or strut head. In other embodiments, the top and/or bottom track mounts can be used to receive a hexagonal head channel bolt 501, as shown in FIGS. 7-10.

In some embodiments, a combination of one or more of top mount 201 and top anchor 203, and/or top anchor 102, and/or top anchor 1910 can be used in conjunction with one or more of bottom mount 202 and bottom anchor 204, and/or bottom anchor 103, and/or bottom anchor 1920.

Figure 4:
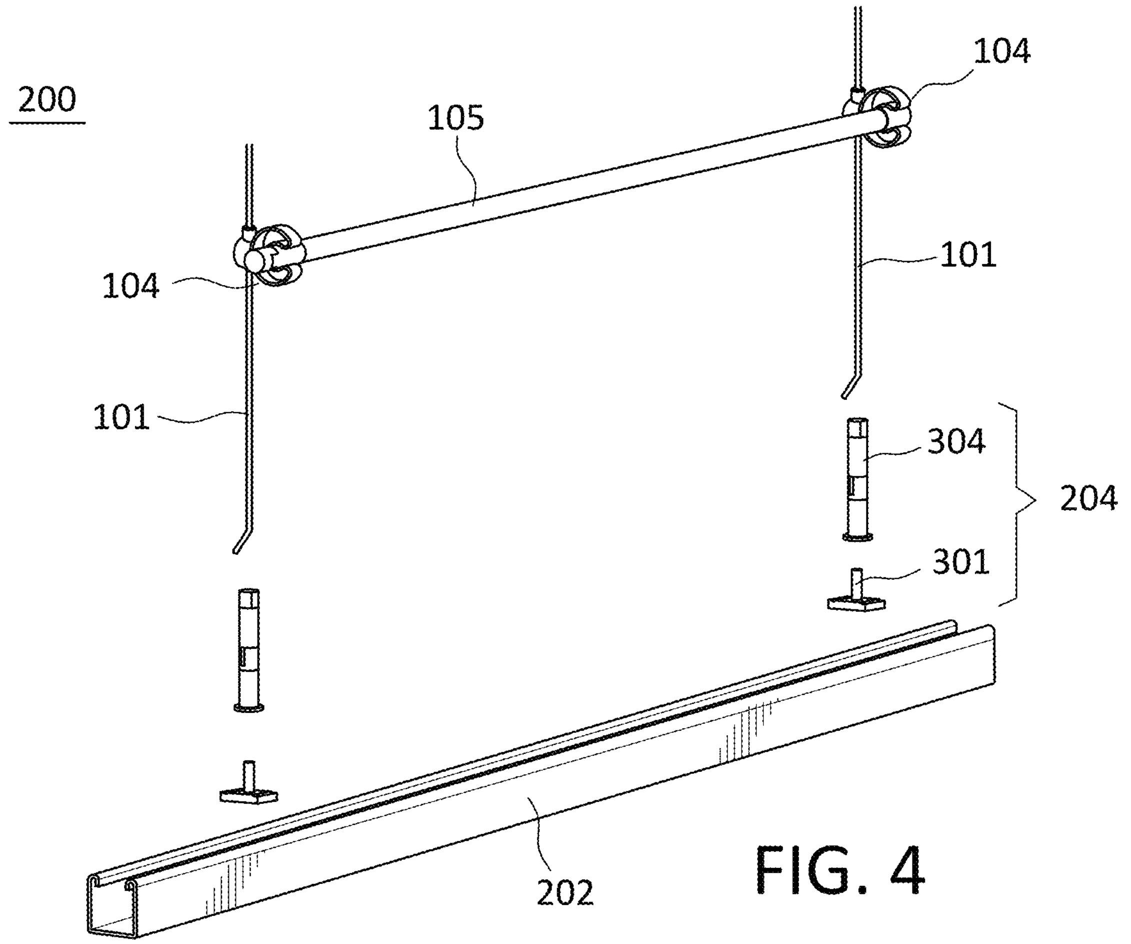
FIG. 4 is an exploded front, left side perspective view of the bottom portion of the cable rack apparatus of FIGS. 2-3.

FIG. 4 shows an exploded view of a bottom portion of cable rack system 200. This exploded view shows one or more cables 101, one or more bottom channel nuts 304, one or more channel bolts 301, one or more clip assemblies 104, UV emitter 105, and bottom mount 202. Together, bottom channel nut 304 and channel bolt 301 comprise bottom anchor 204. In many embodiments, one or more of bottom channel nut 304 and/or channel bolt 301 can be configured to be slidably moveable along bottom mount 202. The width of bottom mount 202 can decrease towards the top of bottom mount 202 to hold channel bolt 301 in place. In other embodiments, channel bolt 301 can be fastened to bottom mount 202. In various embodiments, bottom channel nut 304 can be configured to receive a head portion of channel bolt 301. In this way, a total length of bottom anchor 204 can be adjusted by inserting a larger or smaller portion of channel bolt 301 into bottom channel nut 304. In various embodiments, bottom channel nut 304 can be configured to receive a terminal portion of cable 101. In these embodiments, a lumen of bottom channel nut 304 can be tightened around cable 101 and/or cable 101 can be crimped or knotted so that it remains in bottom channel nut 304. The base of channel bolt 301 can be rectangular or strut shaped as shown in cable rack system 200. In other embodiments, the base of channel bolt 301 may be square, hexagonal, or any other shape.

Figure 5:
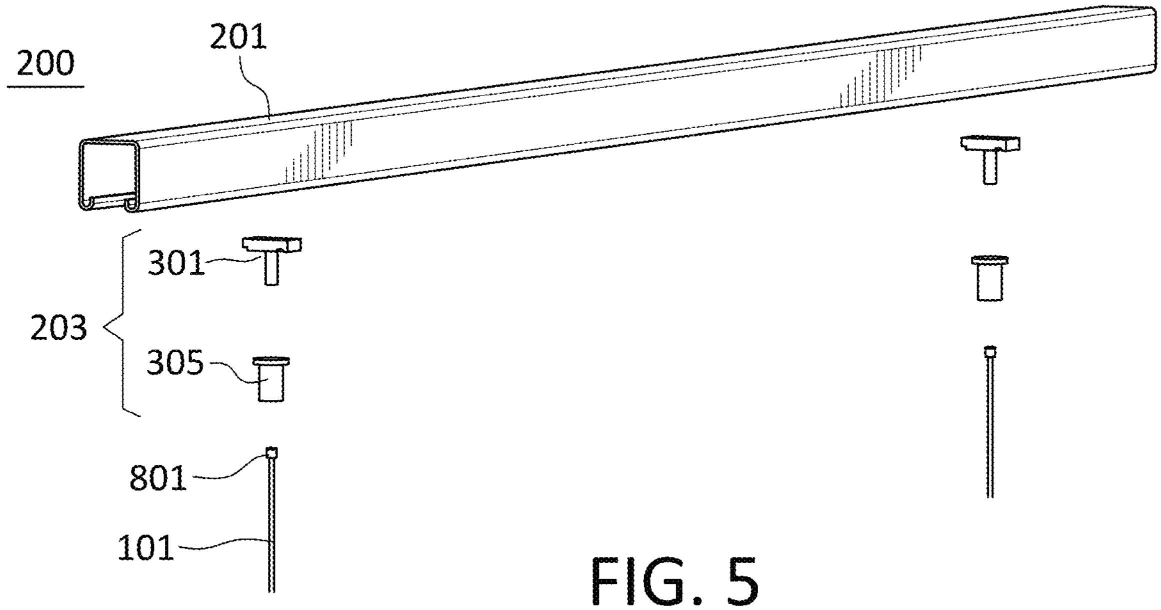
FIG. 5 is a front, left side perspective view of the top portion of the cable rack apparatus of FIGS. 2-3.

FIG. 5 shows an exploded view of a top portion of cable rack system 200. This exploded view shows top mount 201, one or more channel bolts 301, one or more top channel nuts 305, one or more cable shoulders 801, and one or more cables 101. Together, channel bolt 301 and top channel nut 305 comprise top anchor 203. The width of top mount 201 can decrease towards the bottom of top mount 201 to hold channel bolt 301 in place. In many embodiments, one or more of top channel nut 305 and/or channel bolt 301 can be configured to be slidably movable along top mount 201. In other embodiments, channel bolt 301 can be fastened to a top or bottom portion of top mount 201. In various embodiments, top channel nut 305 can be configured to receive a head portion of channel bolt 301. In this way, a total length of top anchor 203 can be adjusted by inserting a larger or smaller portion of channel bolt 301 into top channel nut 305. In various embodiments, top channel nut 305 can be configured to receive a terminal portion of cable 101. In some embodiments, a lumen of top channel nut 305 can be tightened around cable 101 and/or cable 101 can be crimped or knotted so that it remains in top channel nut 305.

Cable 101 can have a cable shoulder 801. Cable shoulder 801 is an area of increased thickness, or diameter, of cable 101. Cable shoulder 801 can be welded, soldered, or fastened to cable 101. In various embodiments, the diameter of cable shoulder 801 is larger than the bottom opening of top channel nut 305 to retain cable shoulder 801 inside of top channel nut 305. The diameter of cable 101 can be smaller than the opening of top channel nut 305 to allow cable 101 to run through top channel nut 305 with cable shoulder 801 anchoring the top end of cable 101 in place. Channel bolts 301 can be coupled to various points along the length of top mount 201. Channel bolts 301 can be spaced farther apart on top mount 201 to accommodate larger UV emitters 105. Channel bolts 301 can be spaced closer together on top mount 201 to accommodate smaller UV emitters 105.

Figure 6:
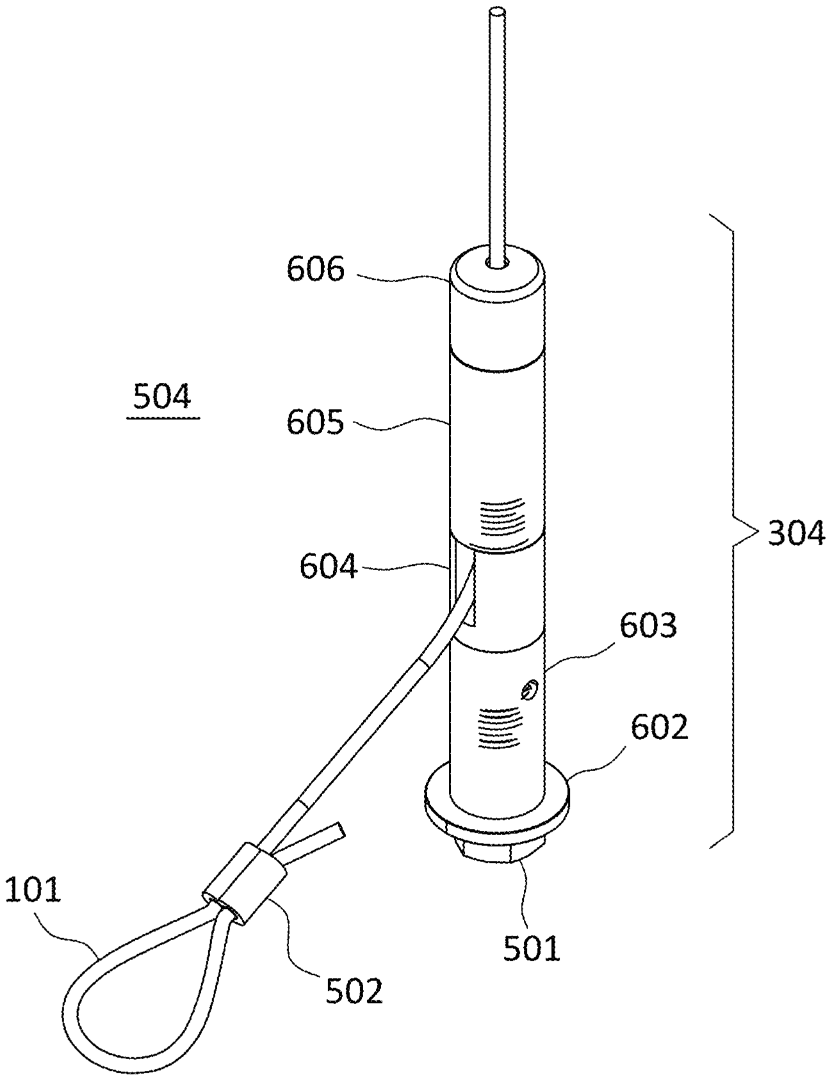
FIG. 6 is an exploded top, front, left side view of a bottom anchor, according to an embodiment of the present invention.

FIG. 6 shows a top, front view of bottom anchor 504. Bottom anchor 504 may be similar or identical to bottom anchor 204. In this embodiment, bottom anchor 504 has a hexagonal bolt head at its base. Bottom anchor 504 comprises bottom channel nut 304 and hexagonal head channel bolt 501. Bottom channel nut 304 includes bottom cap 606, bottom rod 605, slotted bottom surface coupler 604, bottom surface coupler 603, and channel nut 602. The top of bottom cap 606 can be compressed or otherwise engaged to move bottom channel nut 304 along cable 101. In some embodiments, bottom cap 606 can be removed and the remaining components of bottom channel nut 304 can be moved along cable 101 by compressing or otherwise engaging bottom rod 605. In some embodiments, bottom cap 606 and bottom rod 605 can comprise a tensioning mechanism coupled to the one or more cables operable to adjust tension in the one or more cables between the two or more surface mounts. In some embodiments, channel nut 602 can be the tensioning mechanism coupled to the one or more cables operable to adjust tension in the one or more cables between the two or more surface mounts. Tensioning of the system can be achieved by coupling channel nut 602 to the surface. The tensioning mechanism can be coupled to the one or more cables by direct or indirect connection.

Figure 7:
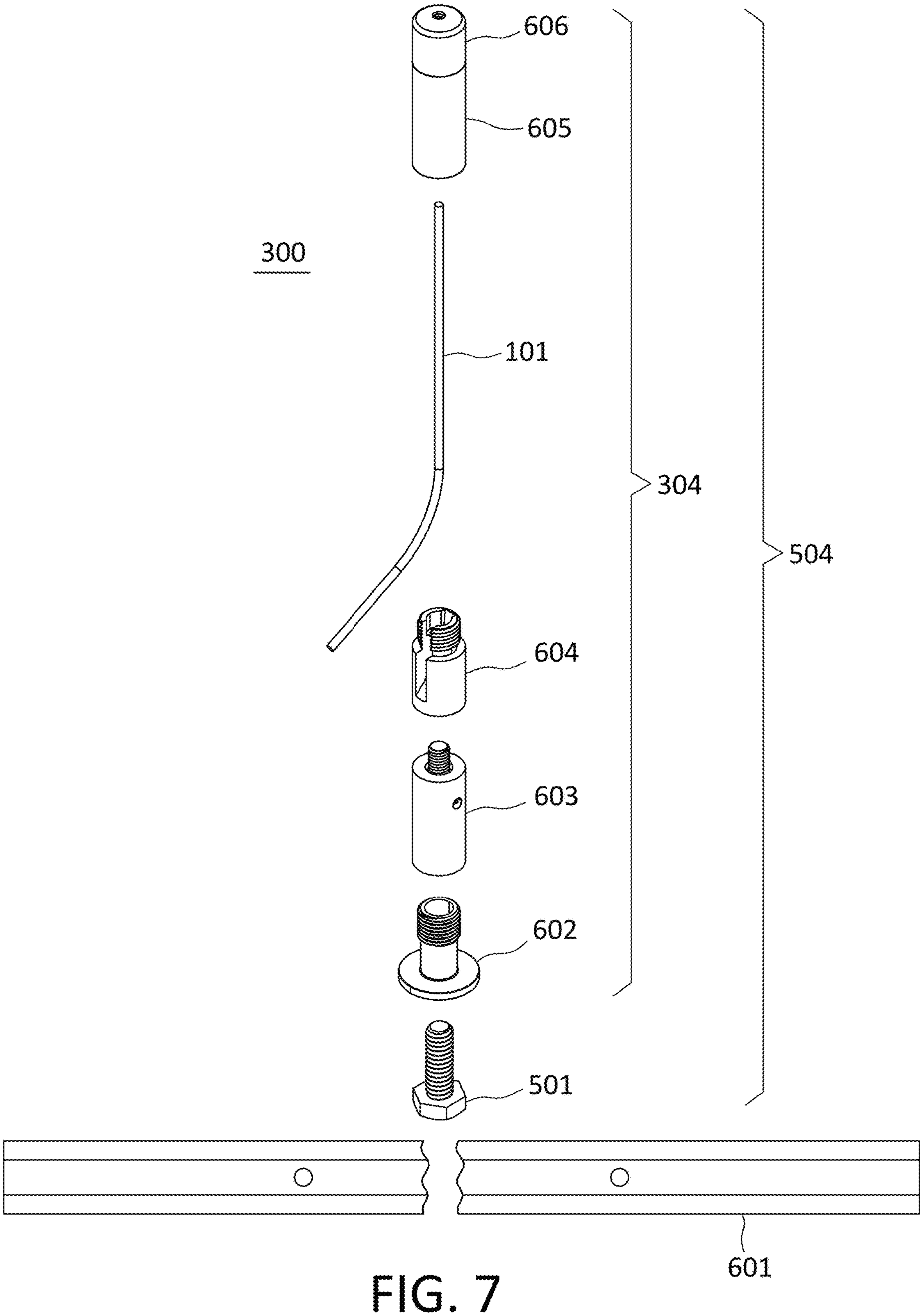
FIG. 7 is an exploded top, front view of the bottom anchor of FIG. 6 and a bottom mount, according to an embodiment of the present invention.

Hexagonal head channel bolt 501 has a head suitable for installation into a mount surface. The view shown in FIG. 6 also shows cable 101 and ferrule 502. Excess cable 101 leaving bottom channel nut 304 can be fed through ferrule 502, formed into a loop, and/or crimped to prevent fraying. Generally, the loop can be formed once the approximate desired tension is achieved between the top and bottom anchors in the cable rack system. Ferrule 502 can be made from metal, plastic, or any other suitable material. Ferrule 502 can prevent excess cable 101 from getting tangled around the cable rack apparatus. Ferrule 502 can also serve as a touch point for the user to tug or pull the cable 101 to increase the tension in the system. The excess cable 101 that can be pulled by the user can extend from the tensioning mechanism or any component coupled thereto (e.g. 602, 1810, 603, 604, 605, and/or 606). Bottom anchor 504 can be secured to bottom mount 601 as shown in FIG. 7 and described below. Bottom mount 601 is configured to receive a hexagonal head channel bolt 501 and can be similar or identical to bottom mount 202, which is configured to receive a rectangular or strut head channel bolt 301.

In the portion of cable rack system 300 shown in FIG. 7, bottom mount 601 is used to receive hexagonal head channel bolt 501. FIG. 7 is a top, front, exploded view of cable rack system 300. This view shows bottom mount 601, hexagonal head channel bolt 501, channel nut 602, bottom surface coupler 603, slotted bottom surface coupler 604, cable 101, bottom rod 605, and bottom cap 606. In some embodiments, hexagonal head bolt 501 extends through bottom mount 601. In some embodiments, the head of hexagonal head bolt 501 can be retained within bottom mount 601 with the shaft of the hexagonal head bolt 501 extending upward of the top of bottom mount 601. In some embodiments, hexagonal head bolt 501 can be slidably movable within bottom mount 601. In other embodiments, hexagonal head bolt 501 can be movable by adjusting the location of fasteners. Channel nut 602 can have internal threads, external threads, and a skirt. The skirt of channel nut 602 can rest on the top of bottom mount 601. The internal threads of channel nut 602 can couple channel nut 602 to the external threads of hexagonal head bolt 501 with bottom mount 601 therebetween. Channel nut 602 can have external threads on the shaft portion of channel nut 602 extending upward from the skirt portion of channel nut 602. The external threads of the shaft of channel nut 602 can be configured to receive the base of bottom surface coupler 603. Bottom surface coupler 603 can have internal threads to couple the base of bottom surface coupler 603 to the shaft portion of channel nut 602. In another embodiment, bottom surface coupler 603 can be fastened, welded, or soldered to channel nut 602. Bottom surface coupler 603 can have a shaft extending from its top portion with external threads configured to couple bottom surface coupler 603 to the bottom of slotted bottom surface coupler 604. Slotted bottom surface coupler 604 can have a slot with a width of sufficient size to allow cable 101 to extend through the slot. Slotted bottom surface coupler 604 can have an external thread on its top portion configured to receive an internal thread of the bottom portion of bottom rod 605. Bottom rod 605 can have an external thread on its top portion configured to receive an internal thread on the bottom portion of bottom cap 606. The top portion of bottom rod 605 and/or bottom cap 606 can be configured to allow the tension between the top anchor and the bottom anchor of the cable rack system to be adjusted.

In another embodiment, the components of bottom channel nut 304 can be manufactured as individual pieces, combination pieces, or as a single piece, as shown in FIG. 8. The ability to manufacture the components in single pieces can facilitate installation and storage. FIG. 8 shows an exploded top, front view of bottom channel nut 304, hexagonal head channel bolt 501, and bottom mount 601. In this view, the component parts of bottom channel nut 304 are shown as a single piece. In other embodiments, the component parts of bottom channel nut 304 include channel nut 602, bottom surface coupler 603, slotted bottom surface coupler 604, bottom rod 605, and bottom cap 606, as shown in FIG. 7. Channel nut 602 can have a skirt that is a rounded, rectangular, square, or any other geometric shape. In yet another embodiment, bottom surface coupler 603 and slotted bottom surface coupler 604 can be fastened or welded together. Slotted bottom surface coupler 604 can have a slot. The slot can be configured to allow the excess cable 101 in the cable rack system (e.g. 100, 200, 300, 400, 600, 700, 800, 3010, 3110) to be released from the side of bottom channel nut 304.

Top anchor assembly 210 shown in FIG. 9 comprises top mount 607, hexagonal head channel bolt 501, top channel nut 305, and set screw 902. Top mount 607 can be similar or identical to top mount 201. Together, hexagonal head channel bolt 501, top channel nut 305, and set screw 902 comprise top anchor 903. In many embodiments, one or more of top channel nut 305 and/or hexagonal head channel bolt 501 can be configured to be slidably movable along top mount 607. In other embodiments, one or more channel bolts 501 can be fastened to portions of top mount 201. In various embodiments, top channel nut 305 can be configured to receive a shaft portion of hexagonal head channel bolt 501. In this way, a total length of top anchor 903 can be adjusted by inserting a larger or smaller portion of hexagonal head channel bolt 501 into top channel nut 305. In various embodiments, top channel nut 305 can be configured to receive a terminal portion of cable 101. In these embodiments, a lumen of top channel nut 305 can be tightened around cable 101 and/or cable 101 can be crimped or knotted so that it remains in top channel nut 305. Set screw 902 is an added safety feature that ensures the system cannot back out over time with the tension applied to cable 101. Set screw 902 can be configured to engage with the shaft of hexagonal head channel bolt 501. One or more set screws 902 can be coupled to the two or more surface mounts (e.g. top anchor 903) to facilitate creating tension along the one or more cables 101 between the two or more surface mounts.

Figure 10:
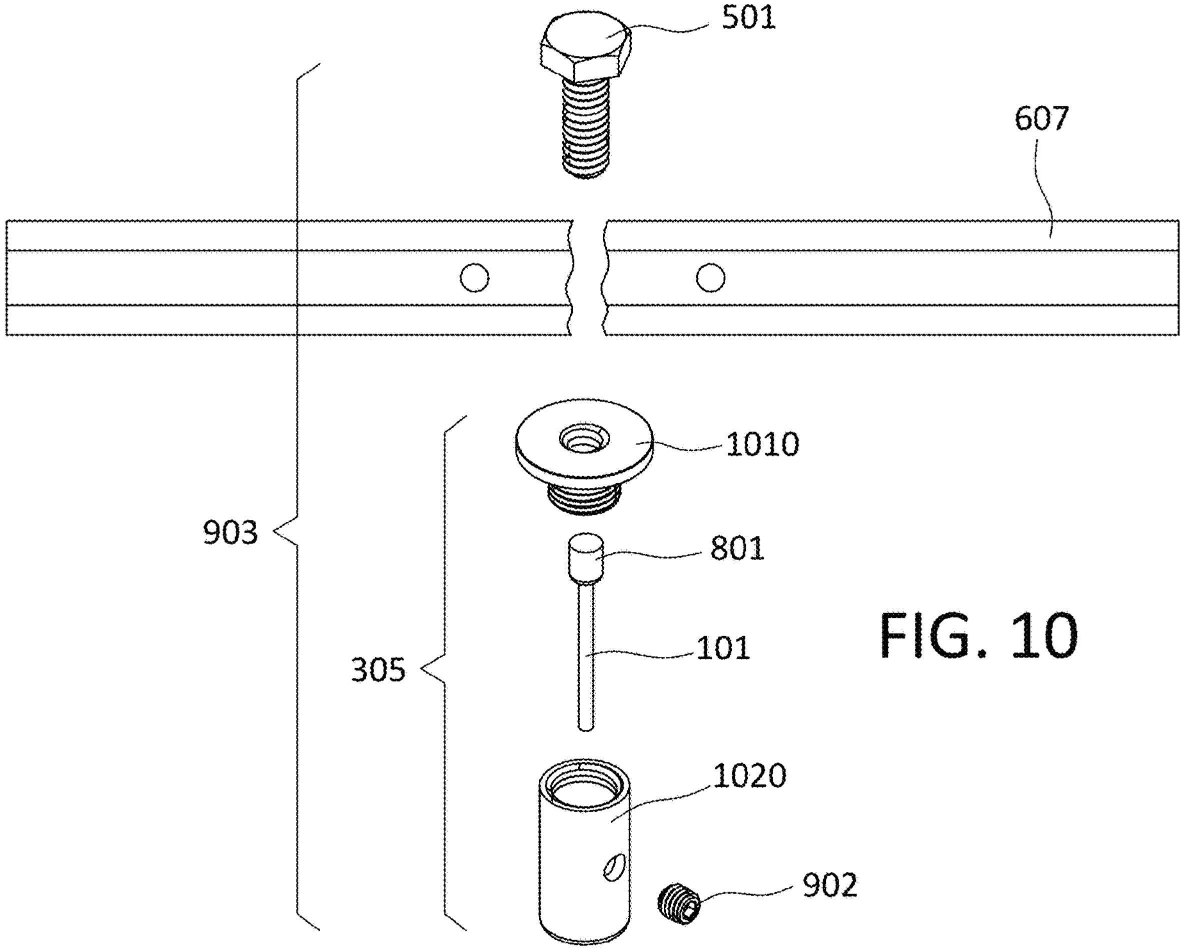
FIG. 10 is an exploded front, top view of the top anchor and the top mount of FIG. 9.

Turning now to FIG. 10 shows an exploded front, top view of the top track mount assembly. In some embodiments, hexagonal head channel bolt 501 can extend through top mount 607. In some embodiments, the head of hexagonal head bolt 501 can be slideably movable within top mount 607 with the shaft of the hexagonal head bolt 501 extending downward of top mount 607. In other embodiments, channel bolt 501 can be fastened to top mount 607. Channel nut 1010 can have internal threads, external threads, and a skirt. The skirt of channel nut 1010 can rest on the bottom of top mount 607. The internal threads of channel nut 1010 can couple channel nut 1010 to the external thread on the shaft of hexagonal head bolt 501 with top mount 607 therebetween. Channel nut 1010 can have external threads on the shaft portion of channel nut 1010 extending downward from the skirt portion of channel nut 1010. The external threads of the shaft of channel nut 1010 can be configured to receive the top portion of top mount coupler 1020. Top mount coupler 1020 can have internal threads to couple the top portion of top mount coupler 1020 to the shaft portion of channel nut 1010. In another embodiment, top mount coupler 1020 can be fastened or welded to channel nut 1010. Top mount coupler 1020 can have one or more apertures on one or more of its sides configured to receive one or more set screws 902. Set screw 902 can be configured to engage with the shaft of hexagonal head channel bolt 501. Top channel nut 305 is comprised of channel nut 1010, top mount coupler 1020, and set screw 902. Top anchor 903 is comprised of top channel nut 305 and hexagonal head channel bolt 501. The view shown in FIG. 10 also shows cable shoulder 801 and cable 101. Cable shoulder 801 is an area of increased thickness, or diameter, of cable 101. Cable shoulder 801 can be welded, soldered, or fastened to cable 101. Cable shoulder 801 can allow the top portion of cable 101 to be retained within top channel nut 305.

Figure 11:
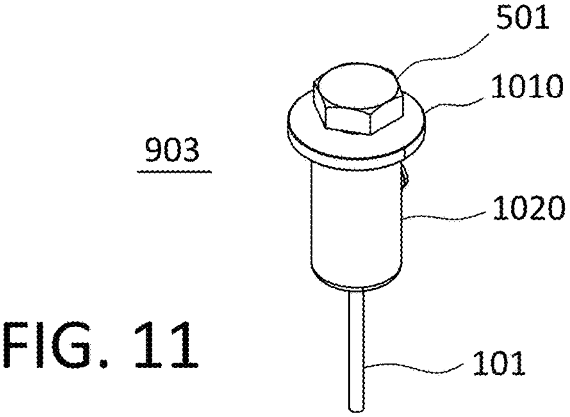
FIG. 11 is a top, front view of the top anchor of FIGS. 9 and 10, according to an embodiment of the present invention.
Figure 16:
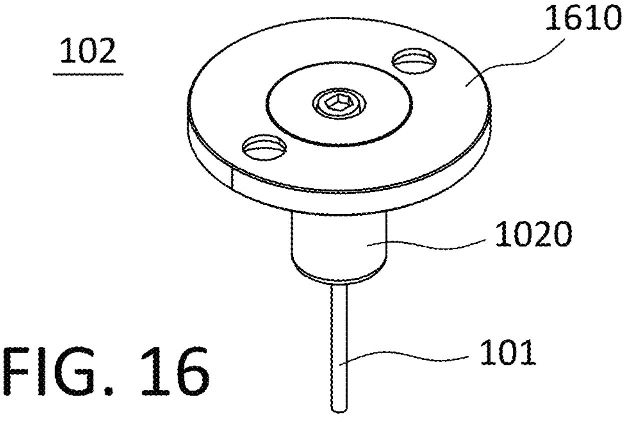
FIG. 16 is a top, front view of the top anchor of FIG. 1.

FIG. 11 shows an assembled view of top anchor 903 which includes hexagonal head bolt 501, channel nut 1010, top mount coupler 1020, and cable 101. In some embodiments, hexagonal head channel bolt 501 can be loosened to slide top anchor 903 into a top mount (e.g. 607) and bolt 501 can be tightened to retain top anchor 903 in place within the top mount (e.g. 607). In some embodiments, top anchor 903 and/or top channel nut 305 can be coupled to top mount coupler 102 for universal mounting applications, as shown in FIG. 16. In other embodiments, top anchors (e.g. 203, 903) can be coupled to top mounts (e.g. 201, 607). Top anchor 203 is similar or identical to top anchor 903. Top anchor 203 generally comprises channel bolt 301 with a rectangular or strut head and top channel nut 305. Top anchor 903 generally comprises hexagonal head channel bolt 501 and top channel nut 305. The head of hexagonal head bolt 501 can be slid between the surfaces of the top mount (e.g. 201, 607). In another embodiment, the shaft of hexagonal head bolt 501 can extend through the top mount (e.g. 201, 607) so that the top mount (e.g. 201, 607) is between the head of hexagonal head bolt 501 and the bottom surface of channel nut 1010.

Figure 17:
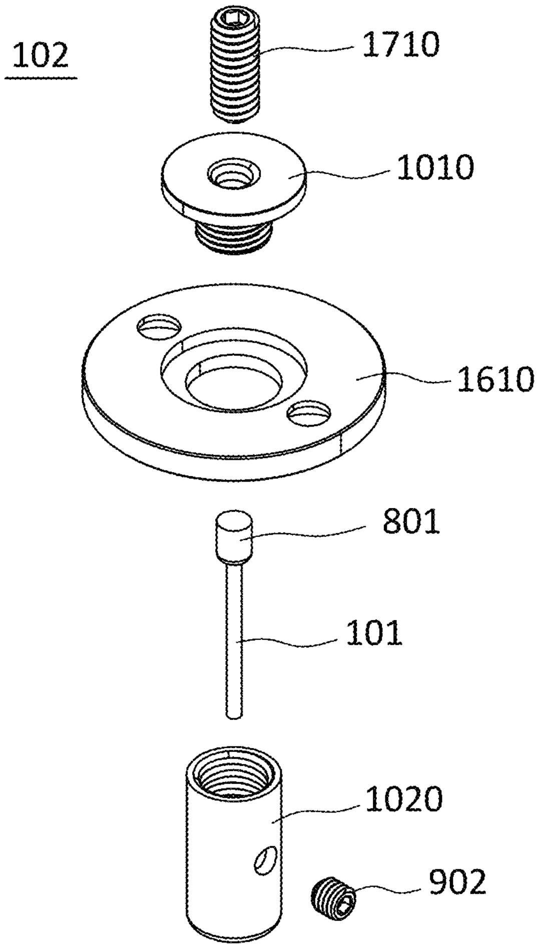
FIG. 17 is a top, front, exploded view of the top anchor of FIGS. 1 and 16.

Jumping ahead in the drawings, FIG. 16 is a top, front view of top anchor 102 showing cable 101, top mount coupler 1020, and universal top mount plate 1610. Universal top mount plate 1610 can have a circular, rectangular, square, or any other geometric shape. In some embodiments, universal top mount plate 1610 may comprise one or more apertures to allow for insertion of one or more fasteners to couple universal top mount plate 1610 to a surface for mounting. FIG. 17 shows an exploded view of top anchor 102. The view includes set screw 1710, channel nut 1010, universal top mount plate 1610, cable shoulder 801, cable 101, top mount coupler 1020, and set screw 902. The external threads of set screw 1710 can couple to the internal threads of channel nut 1010. Channel nut 1010 can have a skirt on its top portion and an external thread on its bottom shaft portion. The external thread of the bottom shaft portion of channel nut 1010 can couple to an aperture near the center of universal top mount plate 1610. The top of channel nut 1010 can be flush with the top surface of universal top mount plate 1610. The top portion of top mount coupler 1020 can have internal threads to couple to the bottom portion of the external threads of channel nut 1010 with the universal top mount plate 1610 therebetween. Set screw 902 can be retained within an aperture on the side of top mount coupler 1020. The set screw 902 can be configured to engage with the set screw 1710. Cable shoulder 801 is an area of increased thickness or diameter, as described above, to retain cable 101 within channel nut 1010 and/or universal top mount plate 1610.

Figure 23:
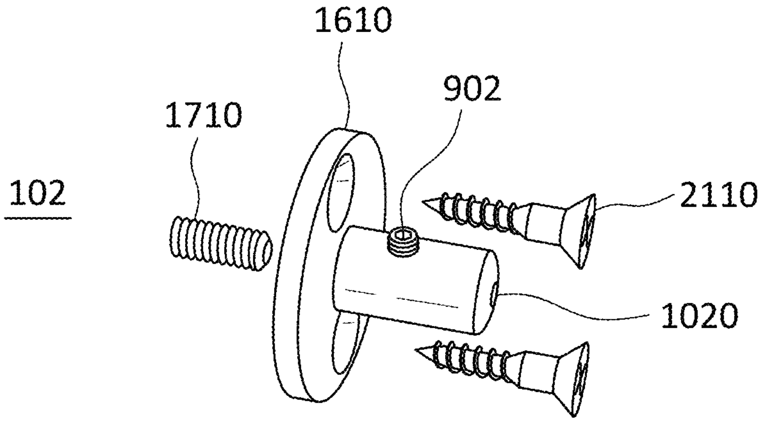
FIG. 23 is a front, left side view of top anchor, universal top mount plates, and set screws of the cable rack apparatus of FIGS. 1, 16, and 17 according to an embodiment of the present invention.

Jumping ahead in the drawings, FIG. 23 shows a left side view of top anchor 102. The view includes set screw 1710, universal top mount plate 1610, top mount coupler 1020, set screw 902, and one or more screw 2110.

Figure 12:
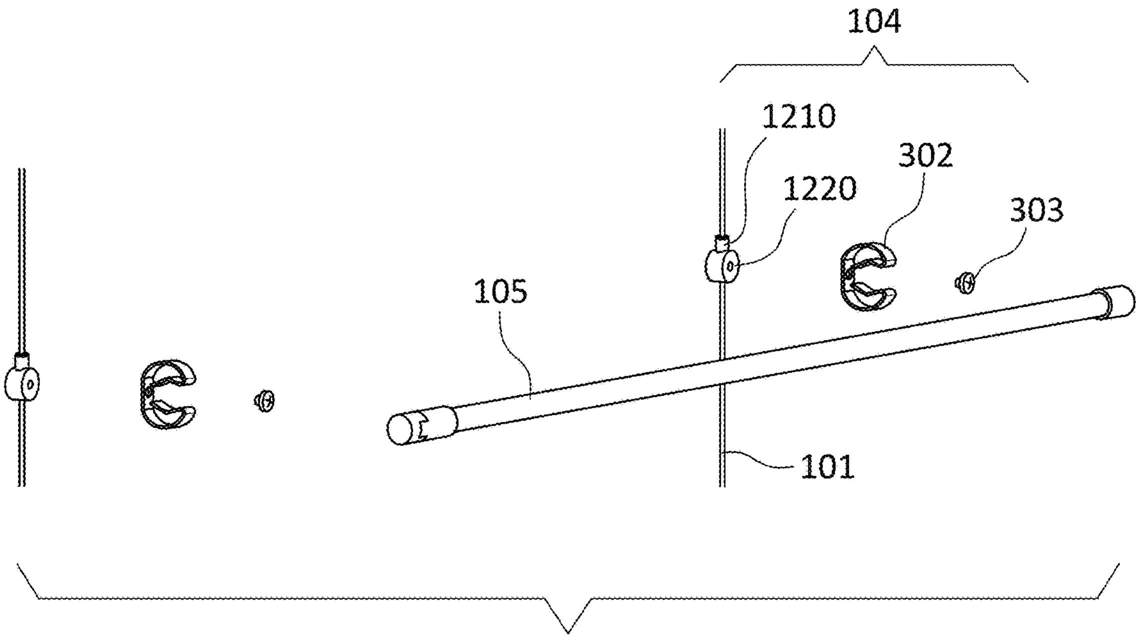
FIG. 12 is an exploded front, left side view of the clip assembly of FIGS. 1-4.
Figure 13:
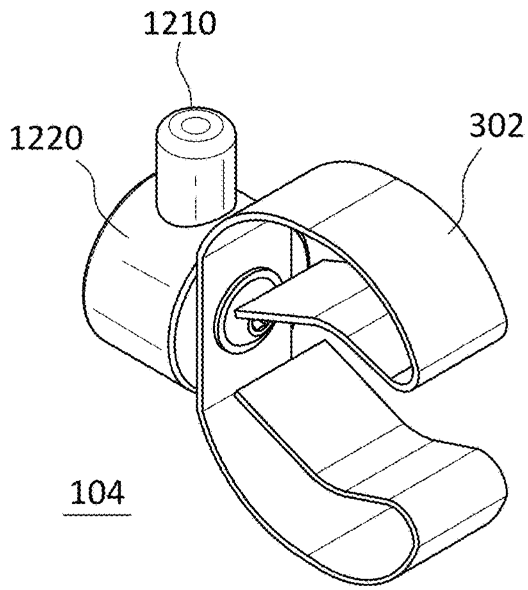
FIG. 13 is a left side view of the clip assembly of FIGS. 1-4.

Turning back in the drawings, clip assembly 104 as shown in FIGS. 12-15 can include cable gripper 1220, cable gripper cap 1210, UV emitter clip 302, and fastener 303. Turning now to FIG. 12, an exploded view of clip assembly 104 is shown. Clip assembly 104 can be configured to receive cable 101 as shown in FIG. 12. In some embodiments, cable gripper 1220 can be configured to slidably receive and hold cable 101. Cable gripper cap 1210 can have an internal thread allowing it to couple to cable gripper 1220. Cable gripper 1220 and/or cable gripper cap 1210 can be a compression mechanism coupled to the one or more UV emitters 105 that allows the position of the one or more UV emitters to be adjusted to alter a distance between the one or more UV emitters and the two or more surface mounts. In various embodiments, an adjustable mechanism of cable gripper 1220 and/or cable gripper cap 1210 can be turned, compressed, depressed, or squeezed to allow adjustment (e.g., sliding) of a position of cable gripper 1220 along cable 101 without using a tool when the adjustable mechanism is engaged. The mechanism can be engaged or compressed by pressing a button, flipping a switch, or engaging some other mechanism to release a component that is preventing the cable gripper 1220 from moving freely along the cable 101. In this way, a location of clip assembly 104 on cable 101 can be adjusted. When an adjustable mechanism of cable gripper 1220 is not activated, the clip assembly 104 can be locked in place along cable 101. In some embodiments, a cable gripper cap 1210 can be secured in place to prevent the adjustable mechanism from being activated inadvertently. An inadvertent activation of the adjustable mechanism can cause fluctuation in the location of UV emitters 105.

In many embodiments, UV emitter clip 302 can be configured to be coupled to UV emitter 105 without damaging UV emitter 105. In some embodiments, UV emitter clip 302 can be heat resistant. In this way, UV emitter clip 302 can grip UV emitter 105 while UV emitter 105 is illuminated without deforming. In various embodiments, one or more clip assemblies 104 can be coupled to one or more cables 101 as shown in FIGS. 1-2. In FIGS. 1-2, one clip assembly 104 couples to the right side of each UV emitter 105 and one clip assembly 104 couples to the left side of each UV emitter 105. In other embodiments, one or more clip assemblies 104 can be coupled to one or more cables 101 such that the UV emitter clip 302 of clip assembly 104 is coupled to the center of one or more UV emitters 105. UV emitter clip 302 can be an over-molded lamp clip made from vinyl or any other suitable material.

UV emitter clip 302 can have a c-type shape or any other shape suitable for retaining UV emitter 105. UV emitter clip 302 can be a fastener configured to receive a UV emitter. In many embodiments, UV emitter clip 302 can be locked in place by tightening fastener 303. In other embodiments, UV emitter clip 302 can rotate freely to allow for adjustments in the orientation of UV emitters 105. In some embodiments, fastener 303 can be configured to couple UV emitter clip 302 to cable gripper 1220. In other embodiments, fastener 303 can couple UV emitter 105 to cable gripper 1220 without using UV emitter clip 302.

In various embodiments, clip assembly 104 can be configured to hold one or more UV emitters 105 and/or join two or more cables together. While FIG. 1 shows each UV emitter 105 held by two clip assemblies 104, it will be understood that a UV emitter can be held by as few as one clip. In these embodiments, a UV emitter can be balanced such that it rests approximately perpendicular to a cable (e.g., with a clip at an approximate midline of the UV emitter or with a UV emitter weighted as to be balanced while coupled to a clip). Additional details about clips useful in a cable racking system are described below. Generally speaking, one or more UV emitters 105 can be configured to sterilize (e.g., inactivating pathogens) air or other gases passing across and/or near to the UV emitter, and/or on heating/cooling coils of an air handling unit or other object. In other embodiments, the UV emitters 105 can be submerged to sterilize liquids passing across and/or near to the UV emitter. The UV emitters of the cable rack system can emit the same or different colors and/or wavelengths. In various embodiments, one or more UV emitters 105 can comprise one or more a UV-B (ultraviolet B, approximately 280 to 315 nanometer wavelength) light emitting diode ("LED"), a UV-C (ultraviolet C, approximately 100 to 280 nanometer wavelength), a UV-A (ultraviolet A, approximately 315-400 nanometer wavelength), a mercury vapor lamp, a pulsing Xenon lamp, an Excimer lamp, and/or another suitable UV emitter. In some embodiments, one or more UV emitters 105 can be an LED board 3410 with one or more LED lights.

Figure 18:
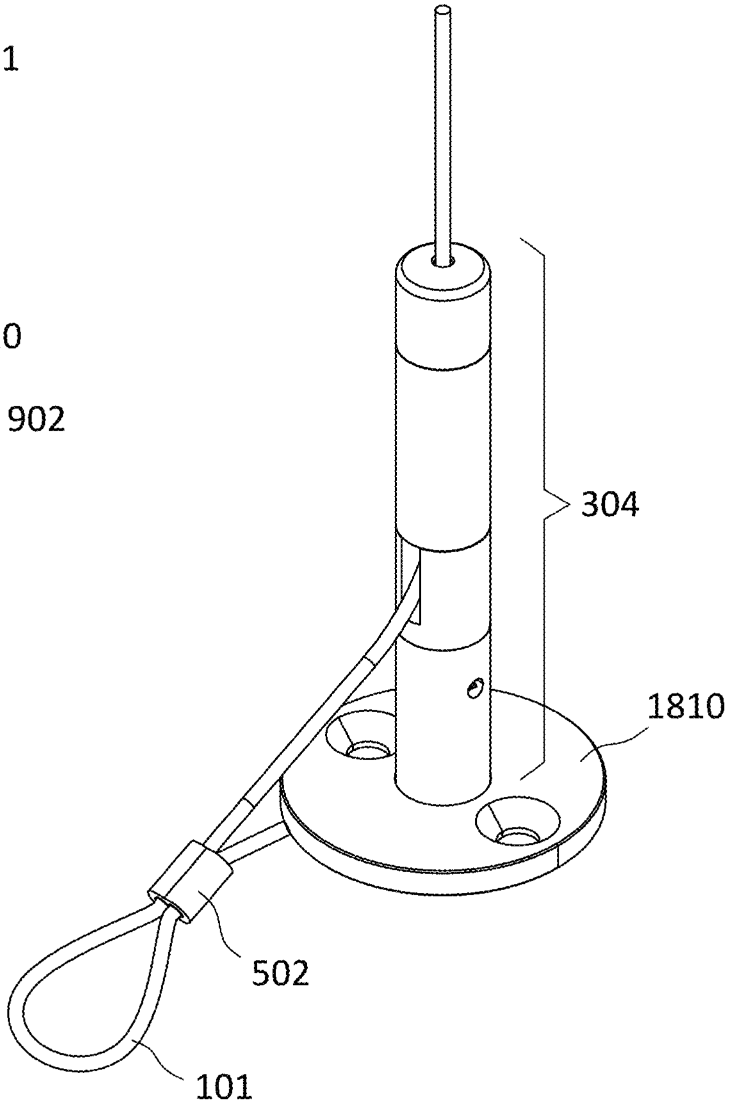
FIG. 18 is a top, front view of the bottom anchor of FIG. 1.
Figure 19:
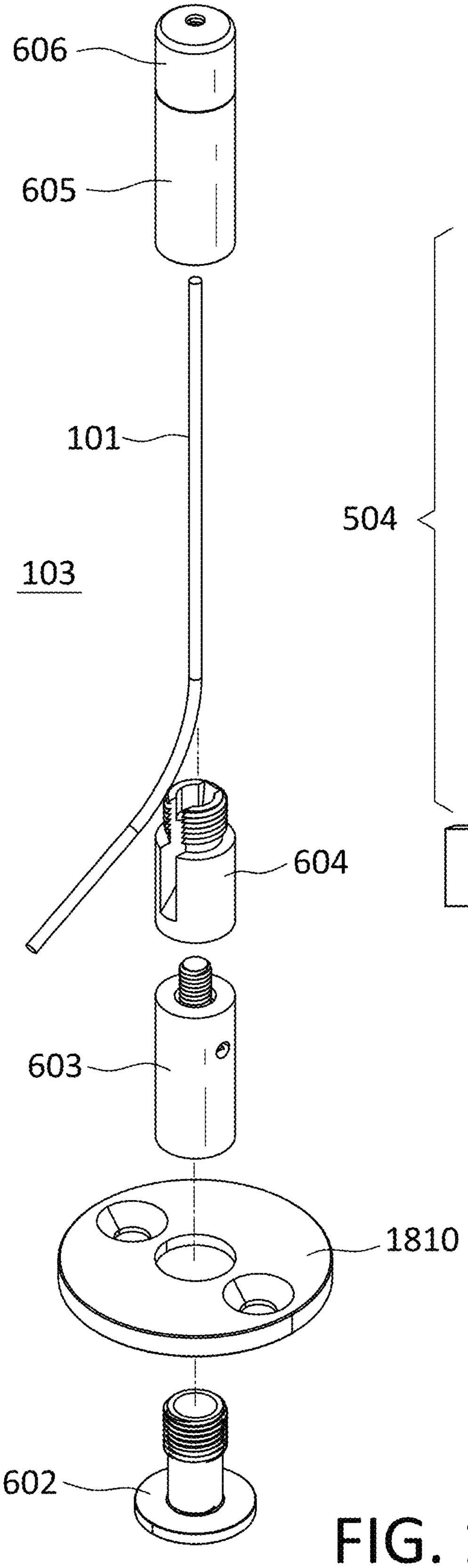
FIG. 19 is a top, front, exploded view of the bottom anchor of FIGS. 1 and 18.

Bottom anchor 103 is shown in FIG. 18 in a top, front view. This view shows universal bottom mount plate 1810, cable 101, ferrule 502, and bottom channel nut 304. Universal bottom mount plate 1810 can include a center aperture for retaining the bottom portion of bottom channel nut 304. Additionally, universal bottom mount plate 1810 can include one or more apertures sized to retain one or more fasteners for mounting bottom anchor 103 to a mounting surface. FIG. 19 is an exploded top, front view of bottom anchor 103. This view shows channel nut 602, universal bottom mount plate 1810, bottom surface coupler 603, slotted bottom surface coupler 604, cable 101, bottom rod 605, and bottom cap 606.

FIG. 20 is a front view of bottom anchor 504. This view shows bottom rod 605, bottom cap 606, slotted bottom surface coupler 604, bottom surface coupler 603, bottom mount 601, cable 101, and ferrule 502. Bottom rod 605 can have an external thread on its top portion allowing it to couple to an internal thread on the bottom portion of bottom cap 606. Bottom rod 605 can have a tensioning mechanism, allowing the cable 101 to move freely through bottom anchor 204 when the tensioning mechanism is engaged or compressed. The tensioning mechanism on the bottom rod 605 can be similar or identical to the adjustable mechanism on the cable gripper 1220. The tensioning mechanism can be engaged by pressing a button, flipping a switch, or engaging some other mechanism to release a component that is preventing the cable 101 from moving freely through bottom anchor 504. In some embodiments, bottom cap 606 can be secured in place to prevent the tensioning mechanism of bottom rod 605 from being inadvertently activated. An inadvertent activation of the tensioning mechanism of bottom rod 605, or other tensioning mechanism, can cause fluctuation in the location of one or more UV emitters 105. In other embodiments, bottom cap 606 can be engaged in a similar or identical manner to bottom rod 605 to adjust the tension in the cable rack system. FIG. 20 depicts bottom rod 605 and bottom cap 606 coupled to bottom mount 601. In another embodiment, bottom rod 605 and bottom cap 606 can be used with bottom mount 202, universal bottom mount plate 1810, bottom anchor 1920, frame 2310, or bottom plate 2520. In yet another embodiment, bottom rod 605 and bottom cap 606 can be coupled to top mount 201, top mount 607, universal top mount plate 1610, top anchor 1910, the top portion of frame 2310, and/or top plate 2510.

Turning now to FIG. 21, a front, left side view of cable rack system 400 is shown. This view shows top anchor 1910 and bottom anchor 1920. Top anchor 1910 is a jointed mount, it can allow the top portion of the cable rack system to be mounted to walls and/or sloped surfaces that are approximately parallel to the orientation of the one or more cables 101. Bottom anchor 1920 is a jointed mount, it can allow the bottom portion of the cable rack system to be mounted to walls and/or sloped surfaces that are approximately parallel to the orientation of the one or more cables 101. Top anchor 1910 can be similar or identical to bottom anchor 1920.

Figure 22:
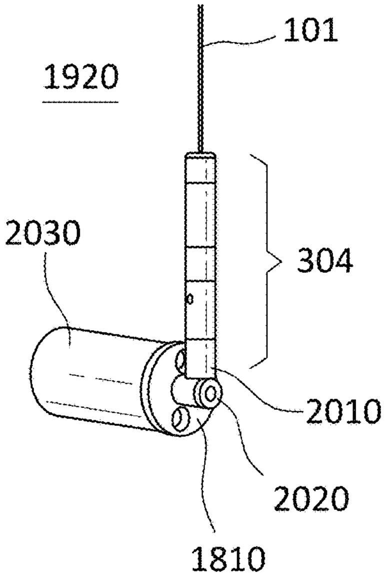
FIG. 22 is a front, left side view of the cable rack apparatus of FIG. 21.

Turning now to FIG. 22, a front, left side view of bottom anchor 1920 is shown. This view shows bottom channel nut 304, jointed mount bottom channel 2010, jointed mount coupler 2020, universal bottom mount plate 1810, cable 101, and jointed mount base 2030. A bottom portion of bottom channel nut 304 can be coupled to a top portion of jointed mount bottom channel 2010. A bottom portion of jointed mount bottom channel 2010 can be coupled to a top portion of jointed mount coupler 2020. In some embodiments, jointed mount bottom channel 2010 and jointed mount coupler 2020 can be formed as a single piece to simplify installation. In other embodiments, jointed mount coupler 2020 can be fastened to jointed mount bottom channel 2010. Jointed mount bottom channel 2010 can rotate about the top portion of jointed mount coupler 2020. A bottom portion of jointed mount coupler 2020 can be retained within an aperture of bottom mount plate 1810. In some embodiments, bottom mount plate 1810 can be coupled to jointed mount base 2030. In some embodiments, a second bottom mount plate 1810 can be used on the bottom of jointed mount base 2030. Jointed mount base 2030 can be circular, rectangular, square, or any other suitable geometric shape. In some embodiments, jointed mount base 2030 is hollow. In other embodiments, jointed mount base 2030 can contain weighted material. In other embodiments, a bottom mount plate 1810 can be coupled to a wall or sloped surface without jointed mount base 2030. Jointed mount base 2030 and/or jointed mount coupler 2020 and/or bottom mount plate 1810 can extend approximately perpendicular to the one or more cables 101 to couple the cable rack system to one or more surfaces approximately parallel to the one or more cables. One or more fasteners can be used to secure a bottom mount plate 1810 to a wall or other surface that is approximately parallel to cable 101. Cable rack system 600 is shown generally in FIG. 24. Cable rack system 600 is merely exemplary, and embodiments of the cable rack system are not limited to the embodiments presented herein. The cable rack system can be employed in many different embodiments or examples not specifically depicted or described herein. Cable rack system 600 can be similar in some respects to 200 (FIG. 2), and various elements of cable rack system 600 can be similar or identical to various elements of cable rack system 200 (FIG. 1). This right side view shows frame 2310, one or more wheels 2320, one or more power source 2330, one or more UV emitters 105, one or more cables 101, one or more clip assemblies 104, one or more bottom channel nuts 304, one or more top channel nuts 305. The frame and wheels allow a user to easily slide the system out from a tight space for maintenance and back into the system when ready to resume use. In a number of embodiments, the frame can slide with or without wheels. The one or more wheels 2320 can be coupled to the bottom portion of the frame 2310. The bottom channel nuts 304 can be coupled to frame 2310 in a variety of different configurations including through channel bolt 301, hexagonal head channel bolt 501, or universal bottom mount plate 1810. Top channel nut 305 can be coupled to frame 2310 in a variety of different configurations including through channel bolt 301, hexagonal head channel bolt 501, or universal top mount plate 1610. It should be understood that cable rack system 600 (and other cable racking systems describe herein) need not be limited to vertical cable installation. In many embodiments, top channel nut 305 and/or bottom channel nut 304 can be affixed to one or more side walls such that cable 101 is oriented horizontally. In a number of embodiments, power cables for the UV emitters (e.g., 2330) can be attached separately to the UV emitters. In some embodiments, the frame 2310 can have less or more than four sides. In some embodiments, cable rack system 600 can include more than one of cable rack system 100, 200, 300, and/or 400. In some embodiments, cable rack system 600 can include one or more frames 2310. In some embodiments, the one or more power source 2330 can be coupled to one or more UV emitters 105 by one or more cables 101.

Figure 25:
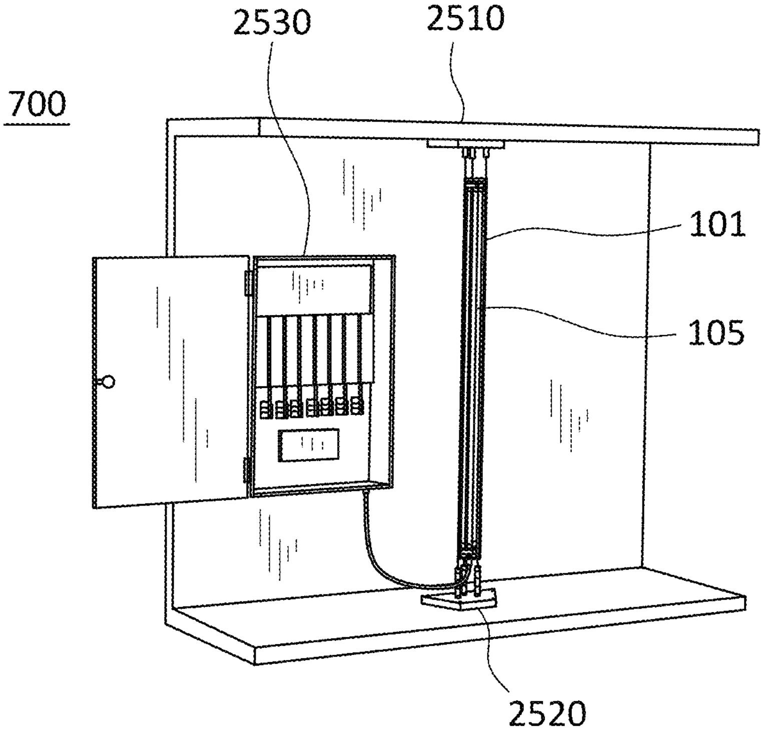
FIG. 25 is a front, left side view of a cable rack apparatus with a power source, top plate, and bottom plate, according to an embodiment of the present invention.

Cable rack system 700 is shown generally in FIGS. 25-28. Cable rack system 700 is merely exemplary, and embodiments of the cable rack system are not limited to the embodiments presented herein. The cable rack system can be employed in many different embodiments or examples not specifically depicted or described herein. Cable rack system 700 can be similar in some respects to 200 (FIG. 2), and various elements of cable rack system 700 can be similar or identical to various elements of cable rack system 200 (FIG. 1). Cable rack system 700 can be used for surface disinfection of plants, flowers, trees and/or any other vertically oriented object. This view shows top plate 2510 coupled to a top surface and bottom plate 2520 coupled to a bottom surface. One or more cables 101 run approximately parallel to one or more UV emitters 105. A power source 2530 is coupled to UV emitters 105 by one or more cables 101. Power source 2530 can include a ballast, relay box for controls, and door as shown in FIGS. 25 and 29. Power source 2530 can be similar or identical to power source 2330. In some embodiments, the door for the power source 2530 can have a magnetic switch for safe access to the cable rack system. Top plate 2510 and bottom plate 2520 can be rectangular, square, circular, triangular, trapezoidal, or any other geometrical shape. Top plate 2510 can be similar or identical to bottom plate 2520.

Figure 26:
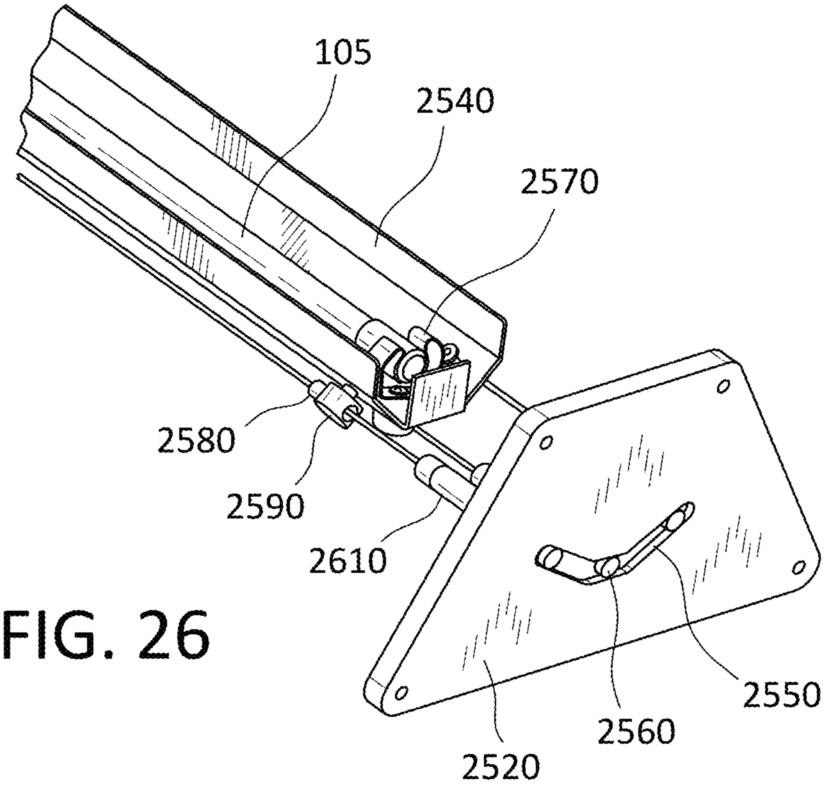
FIG. 26 is a bottom view of the cable rack apparatus of FIG. 25, according to an embodiment of the present invention.

Bottom plate 2520 can have one or more recessed slots 2550 to receive one or more fasteners 2560 as shown generally in FIG. 26. FIG. 26 is a bottom, left side view of cable rack system 700. This view shows bottom plate 2520, slot 2550, one or more fasteners 2560, one or more bottom channel nuts 2610, one or more cables 101, one or more UV emitters 105, reflector 2540, one or more clips 2570, one or more cable grippers 2590, and one or more cable gripper caps 2580. Bottom channel nut 2610 can be similar or identical to bottom channel nut 304. Bottom channel nut 2610 can have a tensioning mechanism that is similar or identical to the tensioning mechanism of bottom channel nut 304 as described above. In some embodiments, one or more fasteners 2560 are used to secure one or more bottom channel nuts 2610 to bottom plate 2520. Cable 101 can be retained within bottom channel nut 2610. In various embodiments, bottom channel nut 2610 can be configured to receive a terminal portion of cable 101 similar to bottom channel nut 304 as described above. In these embodiments, a lumen of bottom channel nut 2610 can be tightened around cable 101 and/or cable 101 can be crimped or knotted so that it remains in bottom channel nut 2610.

Cable gripper 2590 and cable gripper cap 2580 can be similar or identical to cable gripper 1220 and cable gripper cap 1210. In some embodiments, cable gripper 2590 can be coupled to reflector 2540 in one or more locations. In some embodiments, one or more clips 2570 can be coupled to one or more reflectors 2540. In some embodiments, one or more cable grippers 2590 can be coupled to one or more reflectors 2540 and the one or more reflectors 2540 can be coupled to one or more clips 2570 configured to receive one or more UV emitters 105. The one or more clips 2570 can be similar or identical to UV emitter clip 302.

Figure 27:
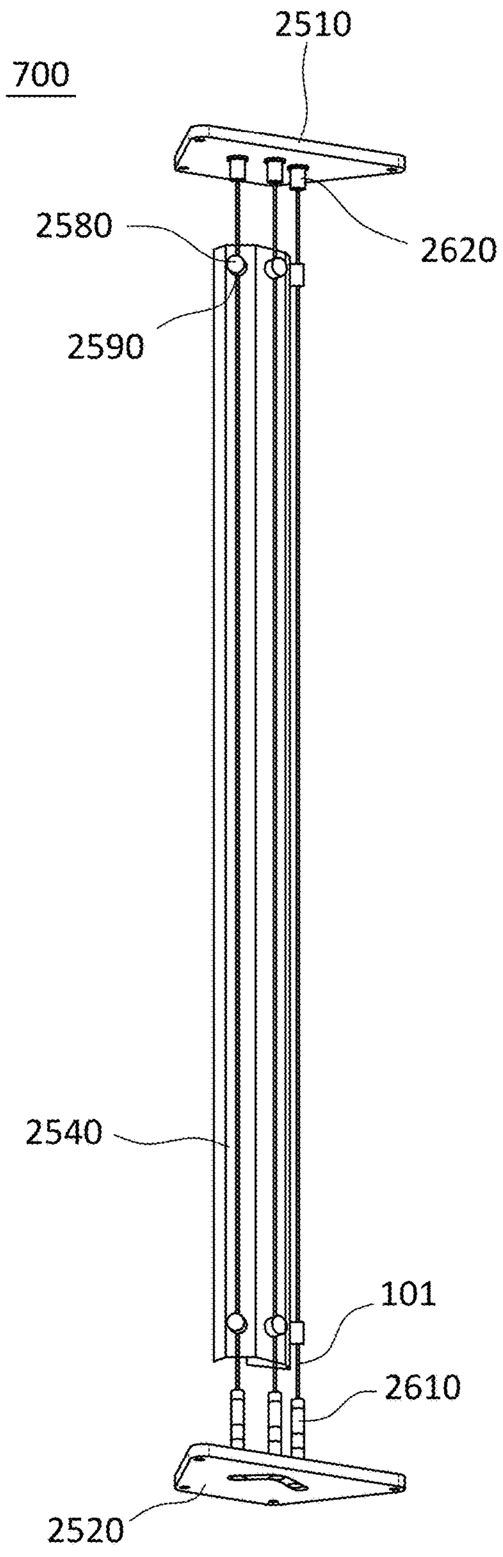
FIG. 27 is a rear view of the cable rack apparatus of FIG. 25, according to an embodiment of the present invention.

FIG. 27 is a back, rear view of cable rack system 700. This view shows the back side of reflector 2540, one or more cables 101, one or more cable grippers 2590, one or more cable gripper caps 2580, one or more top channel nuts 2620, one or more bottom channel nuts 2610, top plate 2510, and bottom plate 2520. One or more cable grippers 2590 are coupled to the back side of reflector 2540. One or more cables 101 run through top channel nut 2620, one or more top cable gripper caps 2580, one or more top cable grippers 2590, one or more bottom cable gripper caps 2580, one or more bottom cable grippers 2590, and one or more bottom channel nuts 2610. Cable gripper caps 2580 and cable grippers 2590 can move along cable 101 to couple to different spots on reflector 2540. The ability to move cable gripper caps 2580 and cable grippers 2590 allows the cable rack system to accommodate different size UV emitters.

Figure 28:
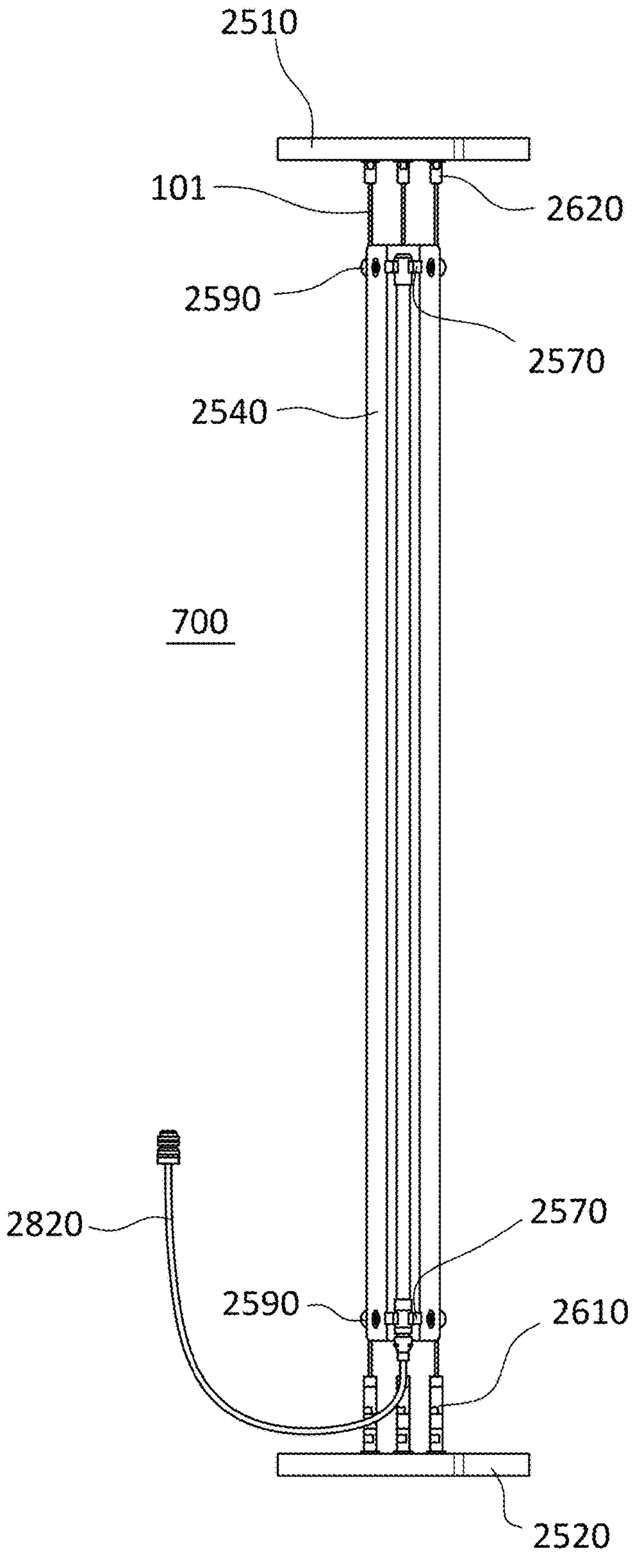
FIG. 28 is a side view of the cable rack apparatus of FIG. 25, according to an embodiment of the present invention.
Figure 29:
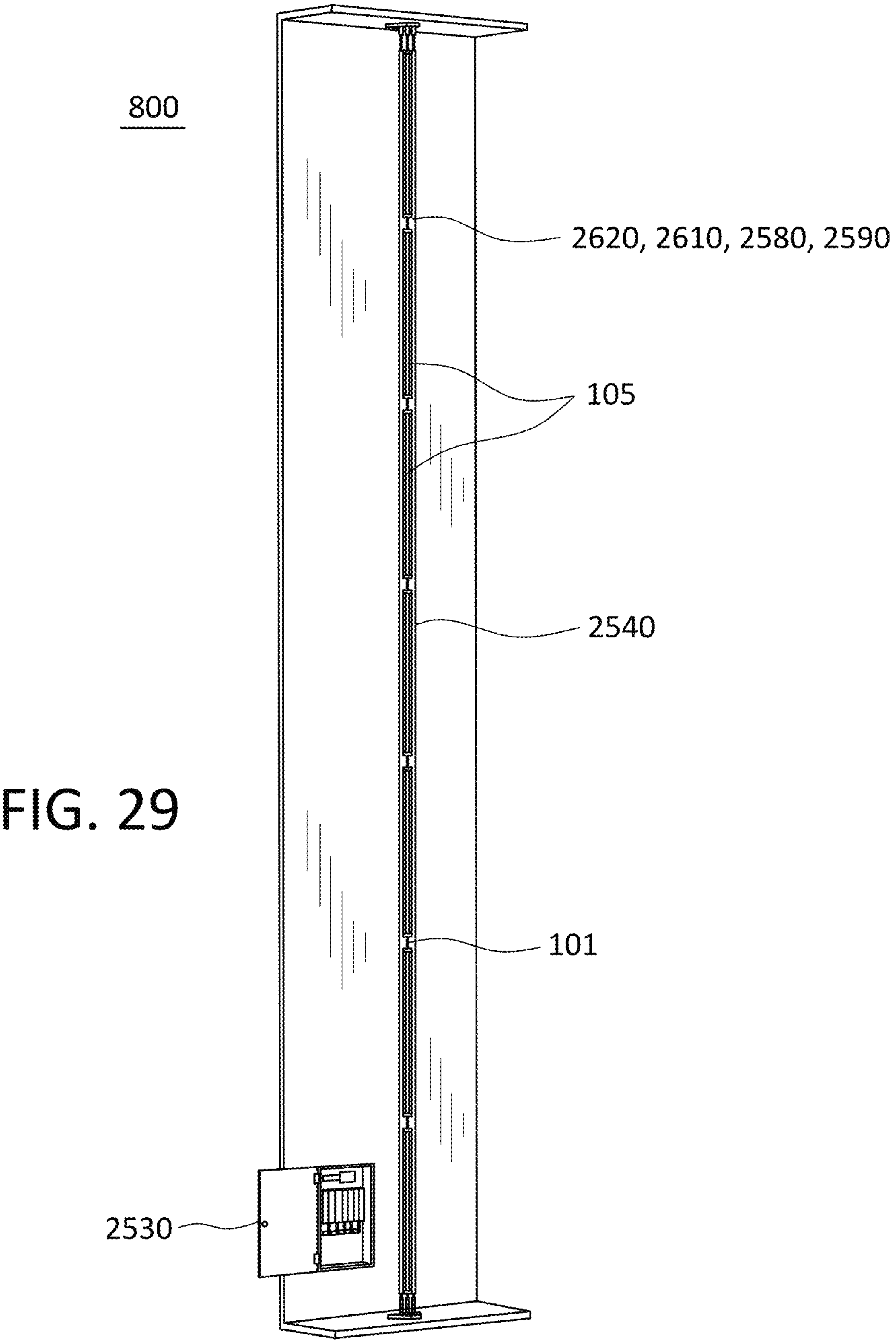
FIG. 29 is a front, left side view of a cable rack apparatus with UV emitters stacked vertically, according to an embodiment of the present invention.

FIG. 28 is a front view of cable rack system 700. This view shows a reflector 2540 with three cables 101 coupled to its back side. The three cables are coupled to top plate 2510 by three top channel nuts 2620. The three cables are coupled to the bottom plate 2520 by three bottom channel nuts 2610. Three cable grippers 2590 are coupled to the top and bottom portions of reflector 2540. The cable grippers 2590 coupled to the top and bottom, center portions of reflector 2540 are coupled to clips 2570. The cable grippers 2590 coupled to the right and left side portions of the top and bottom of reflectors 2540 can be coupled to a fastener or the right and left sides of clips 2570. The cable gripper 2590 coupled to the center portion of the top or bottom of reflector 2540 can be coupled to a clip 2570 and/or a cable 2820 that can be coupled to a power source. Cables 101 can run approximately parallel to reflector 2540.

FIG. 29 is a front view of cable rack system 800. Cable rack system 800 is merely exemplary, and embodiments of the cable rack system are not limited to the embodiments presented herein. The cable rack system can be employed in many different embodiments or examples not specifically depicted or described herein. Cable rack system 800 can be similar in some respects to 200 (FIG. 2), and various elements of cable rack system 800 can be similar or identical to various elements of cable rack system 800 (FIG. 1). Some embodiments include one or more UV emitters 105 stacked vertically as shown generally in FIG. 29. Stacking lamps vertically with one or more reflectors 2540 allows the system to be scaled for use with objects of varying height. In some embodiments, one or more UV emitters 105 can be coupled together using one or more top channel nuts 2620 and/or one or more bottom channel nuts 2610 and/or one or more cable grippers 2590 with one or more cable gripper caps 2580. The tension in the cable 101 can be adjusted to accommodate different sizes and numbers of UV emitters 105. In some embodiments, one or more cable grippers 2590 and cable gripper caps 2580 can be used in between the one or more UV emitters 105 to adjust the tension between the one or more UV emitters 105 and/or to allow the system 800 to accommodate UV emitters 105 of different lengths. In another embodiment, one or more bottom channel nuts 2610 can be used in between the one or more UV emitters 105 to adjust the tension between the one or more UV emitters 105 and/or to allow the system 800 to accommodate UV emitters 105 of different lengths.

Figure 24:
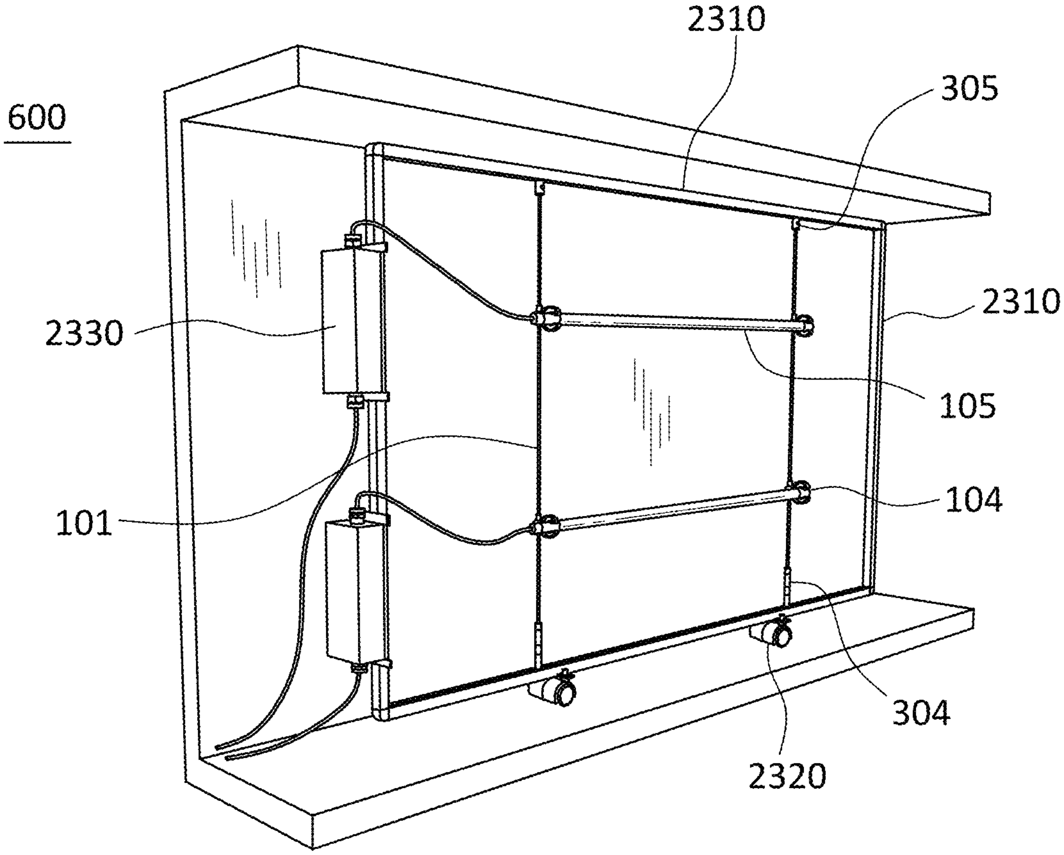
FIG. 24 is a front, left side view of a cable rack apparatus with a frame, power source, and wheels, according to an embodiment of the present invention.
Figure 30:
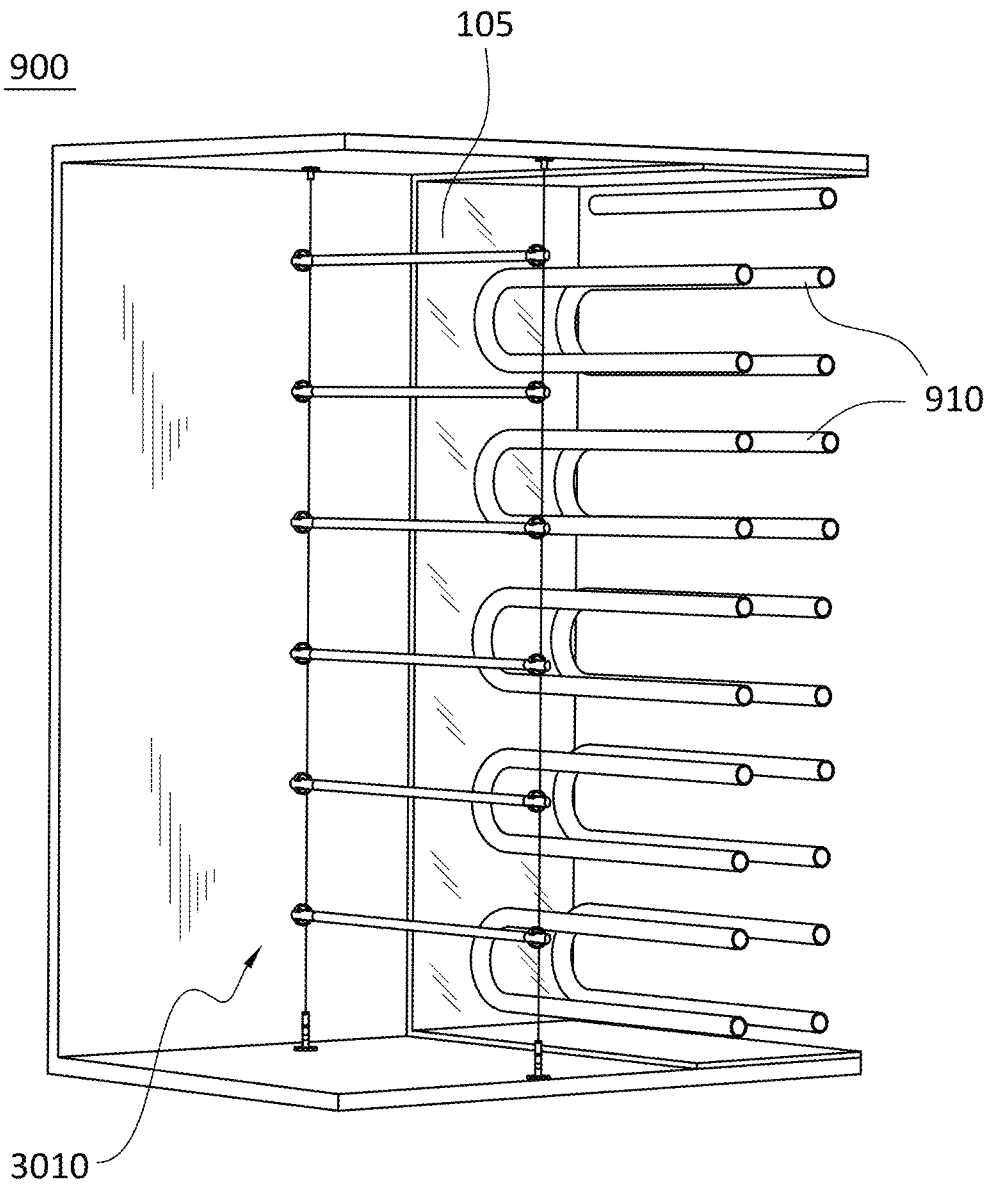
FIG. 30 is a front, right side view of a cable rack apparatus, according to an embodiment of the present invention, used in conjunction with an HVAC system.
Figure 31:
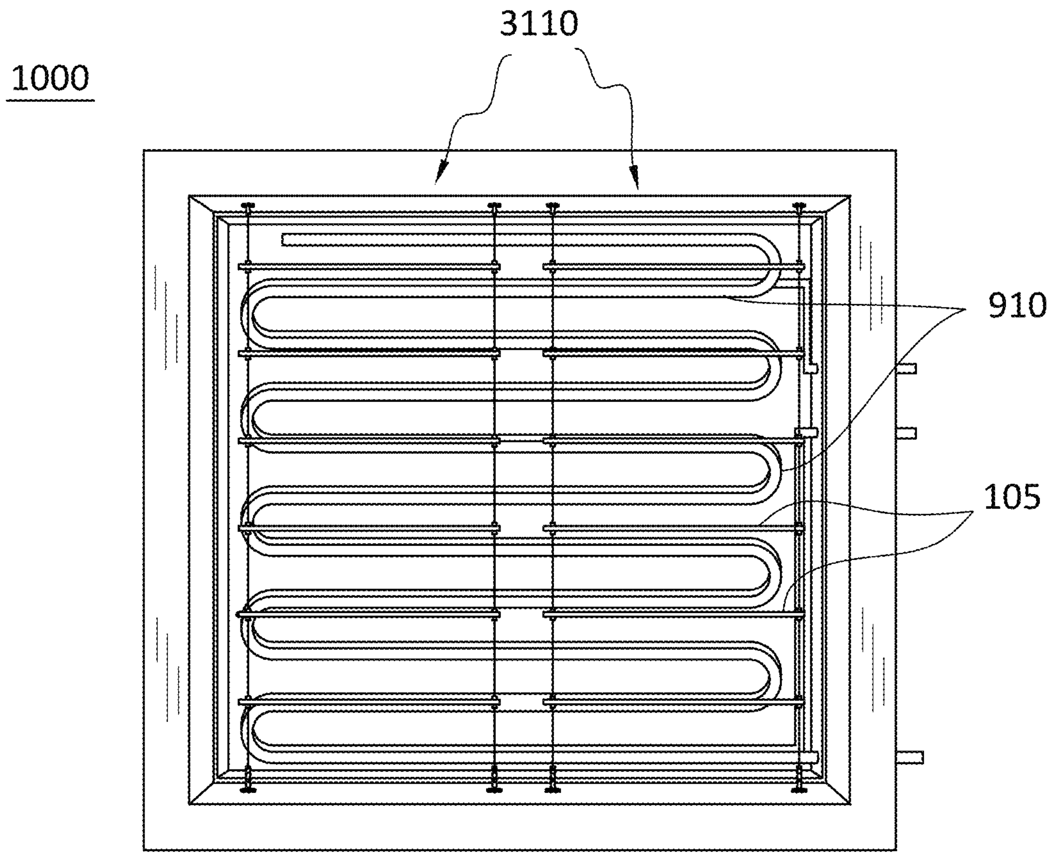
FIG. 31 is a front view of a cable rack apparatus, according to an embodiment of the present invention, used in conjunction with an HVAC system.

Turning now to FIGS. 30 and 31, exemplary air handling systems 900 and 1000 are shown. Air handling systems 900 and 1000 can be specifically designed to disinfect the air and coils in an HVAC (Heating, Ventilation, Air Conditioning) systems. Moving air from the HVAC system will pass over UV emitters 105 inactivating pathogens in air flow. UV emitters 105 can also irradiate on heating/cooling coils 910 inactivating any pathogens growing on coil surface. Some Air Handling Units have limited access to the coils 910 and therefore make it a challenge to have a technician enter the space and have enough room to build or service a racking system. In some embodiments, the cable rack system 600 as shown in FIG. 24 can be suspended between a frame 2310 with wheels 2320 and rolled into the space. This enables users to easily slide the frame 2310 and cable rack system 600 out from the tight space for any maintenance and slide the frame 2310 and cable rack system 600 back in the space.

In various embodiments, air handling systems 900 and 1000 can comprise cable rack systems 3010 and/or 3110. Cable rack systems 3010 and/or 3110 can be similar or identical to cable rack systems 100 (FIG. 1), 200 (FIGS. 2-5), 300 (FIGS. 6-10), 400 (FIG. 21), 600 (FIG. 24), 700 (FIGS. 25-28), and/or 800 (FIG. 29). In many embodiments, air handling systems 900 and 1000 can be used in conjunction with an HVAC system. As shown in FIG. 31, multiple cable rack systems (e.g., 3110) can be installed in air handling system 1000 at various points. For example, cable rack system 3010 and/or 3110 can be installed in between a prefilter and a cooling coil and/or a cable rack system 3010 and/or 3110 can be installed between a cooling coil and fans. In this way, air can be sterilized one or more times as it passes through the air handling system (e.g., 900 and/or 1000). In other embodiments, the cable rack systems can be installed in roof top units, which can be similar to air handling system (e.g., 900 and/or 1000).

Figure 32:
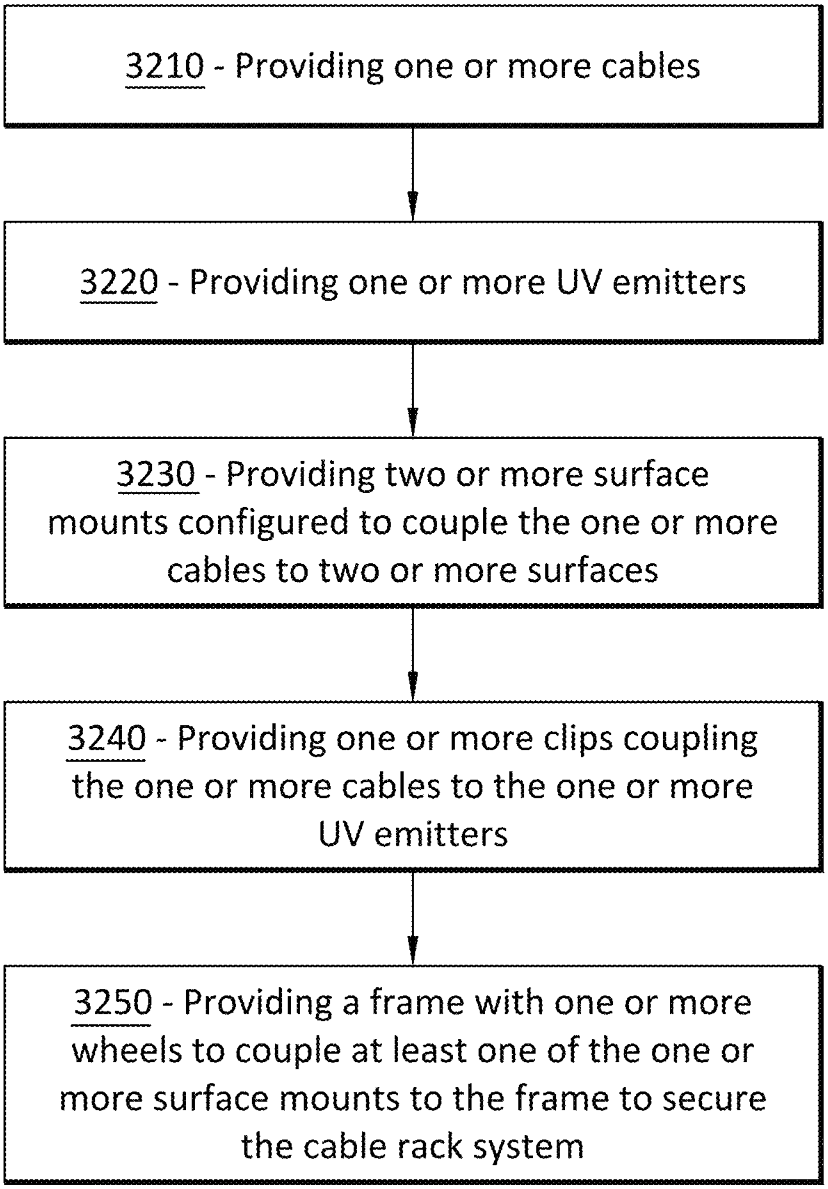
FIG. 32 is a flow chart of a method for providing a cable rack system.

Turning ahead in the drawings, FIG. 32 illustrates a flow chart for a method 3200 of providing cable rack system, according to an embodiment. The cable rack system can be similar or identical to cable rack systems 100, 200, 300, 400, 600, 700, 800, 3010, 3110 and/or 1100. Method 3200 is merely exemplary and is not limited to the embodiments presented herein. The method can be employed in many different embodiments or examples not specifically depicted or described herein. In some embodiments, the procedures, the processes, and/or the activities of method 3200 can be performed in the order presented. In other embodiments, the procedures, the processes, and/or the activities of method 3200 can be performed in any suitable order. In still other embodiments, one or more of the procedures, the processes, and/or the activities of method 3200 can be combined or skipped.

Referring to FIG. 32, method 3200 can include an activity 3210 of providing one or more cables. The one or more cables can be similar or identical to cables 101. In a number of embodiments, method 3200 also can include an activity 3220 of providing one or more UV emitters. The one or more UV emitters can be similar or identical to UV emitters 105. In some embodiments, method 3200 can also include an activity 3230 of providing two or more surface mounts configured to couple the one or more cables to two or more surfaces. The surface mounts can be similar or identical to top anchors (e.g. 102, 203, 903, 1910) or bottom anchors (e.g. 103, 204, 504, 1920). In some embodiments, method 3200 can also include an activity 3240 of providing one or more clips coupling the one or more cables to the one or more UV emitters. The one or more clips can be similar or identical to clip assemblies 104. In some embodiments, method 3200 can also include an activity 3250 of providing a frame with one or more wheels to couple at least one of the one or more surface mounts to the frame to secure the cable rack system. The frame can be similar or identical to frame 2310. The wheels can be similar or identical to wheels 2320.

Figure 33:
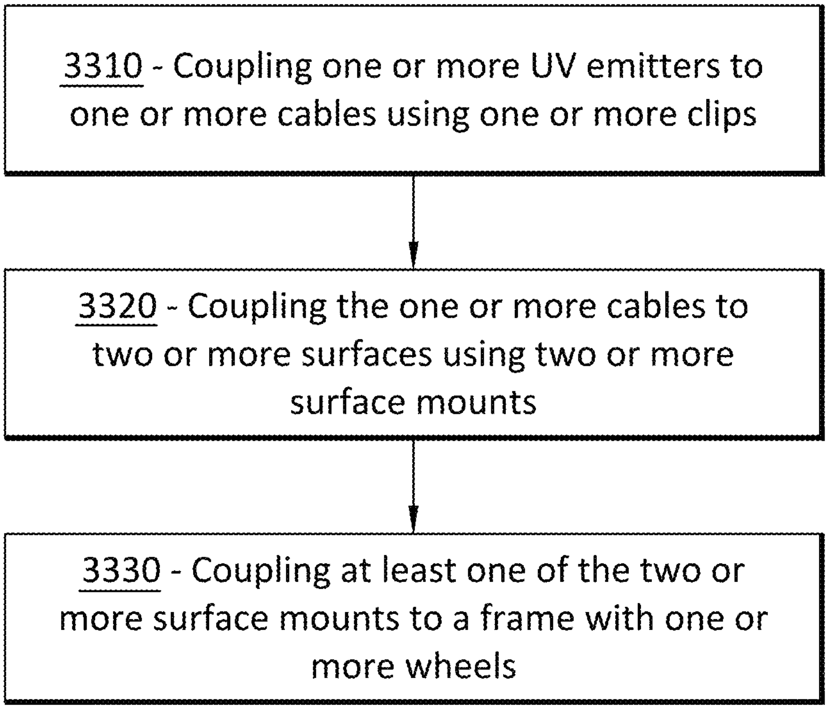
FIG. 33 is a flow chart of a method for installing a cable rack system.

Turning ahead in the drawings, FIG. 33 illustrates a flow chart for a method 3300 of installing a cable rack system. The cable rack system can be similar or identical to cable rack systems 100, 200, 300, 400, 600, 700, 800, 3010, 3110, and/or 1100. Method 3300 is merely exemplary and is not limited to the embodiments presented herein. The method can be employed in many different embodiments or examples not specifically depicted or described herein. In some embodiments, the procedures, the processes, and/or the activities of method 3300 can be performed in the order presented. In other embodiments, the procedures, the processes, and/or the activities of method 3300 can be performed in any suitable order. In still other embodiments, one or more of the procedures, the processes, and/or the activities of method 3300 can be combined or skipped. Method 3300 can include an activity 3310 of coupling one or more UV emitters to one or more cables using one or more clips. The clips can be similar or identical to UV emitter clips 302. In some embodiments, method 3300 can include an activity 3320 of coupling the one or more cables to two or more surfaces using two or more surface mounts. The surface mounts can be similar or identical to top anchors (e.g. 102, 203, 903, 1910) or bottom anchors (e.g. 103, 204, 504, 1920). In some embodiments, method 3300 can include an activity 3330 of coupling at least one of the two or more surface mounts to a frame with one or more wheels. The frame can be similar or identical to frame 2310. The wheels can be similar or identical to wheels 2320.

Figure 34:
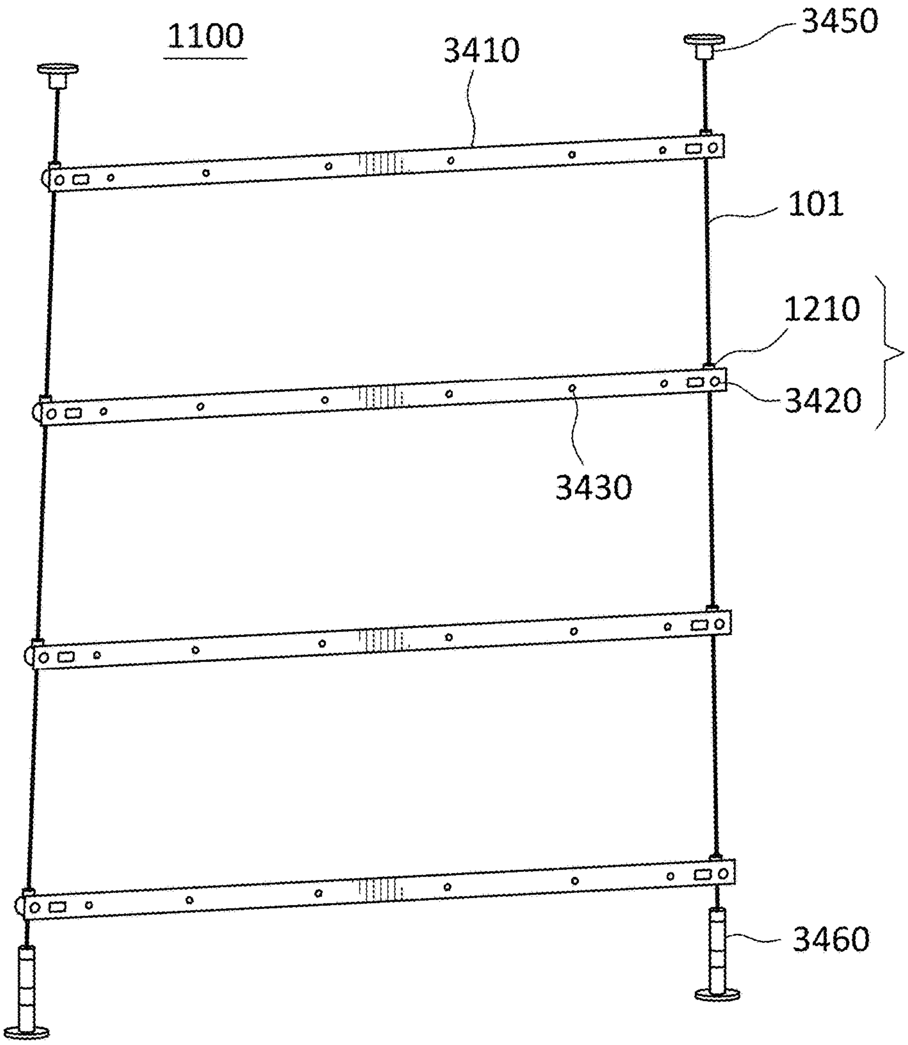
FIG. 34 is a front, side view of a cable rack apparatus with LED boards, according to an embodiment of the present invention.

FIG. 34 is a front view of cable rack system 1100. Cable rack system 1100 can include one or more cables 101, one or more LED boards 3410, one or clip assemblies 3440, and one or more apertures 3430. Clip assembly 3440 can comprise fastener 3420, cable gripper cap 1210, and cable gripper 1220 (shown in FIG. 35). Top anchor 3450 can be similar or identical to top anchors 203, 903, 102, 1910 described above. Bottom anchor 3460 can be similar or identical to bottom anchors 103, 504, 1920, 204 described above. The LED board 3410 can have one or more apertures 3430. The one or more apertures 3430 can allow for one or more cables 101 to be coupled to different locations on the LED board 3410. The one or more clip assemblies 104 can be coupled to the one or more cables 101. Top anchor 3450 and bottom anchor 3460 can be surface mounts configured to couple the one or more cables 101 to one or more surfaces. In some embodiments of cable rack system 1100, one or more LED boards 3410 can be used with one or more UV emitters 105. An LED board 3410 can have one or more LED lights.

Figure 14:
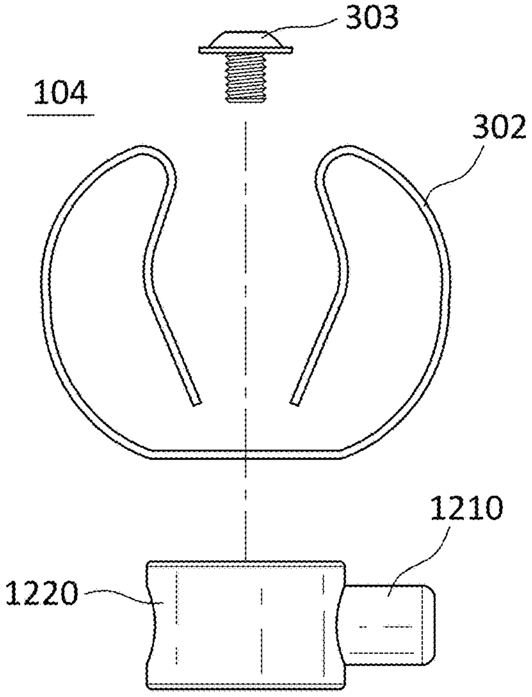
FIG. 14 is an exploded view of the clip assembly of FIGS. 1-4.
Figure 15:
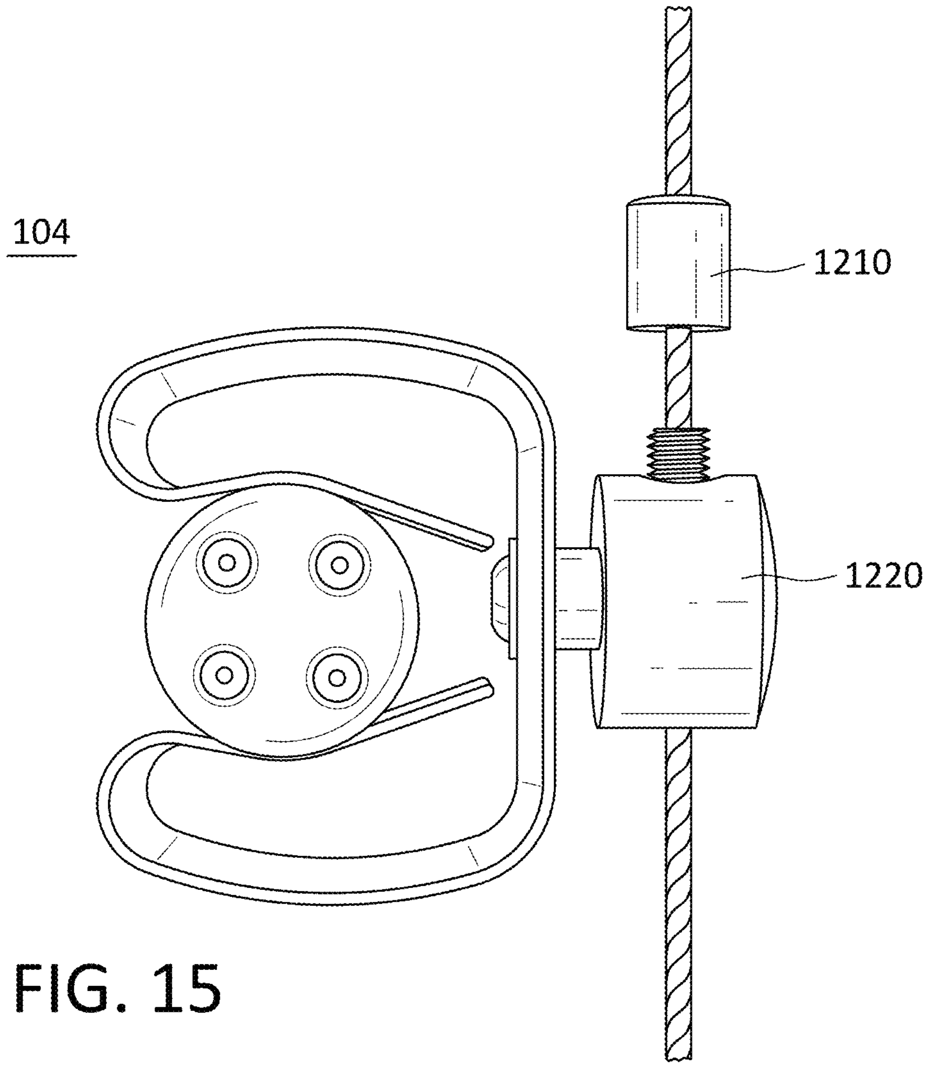
FIG. 15 is a side view of the clip assembly of FIGS. 1-4 with the cable gripper cap in the detached position.
Figure 35:
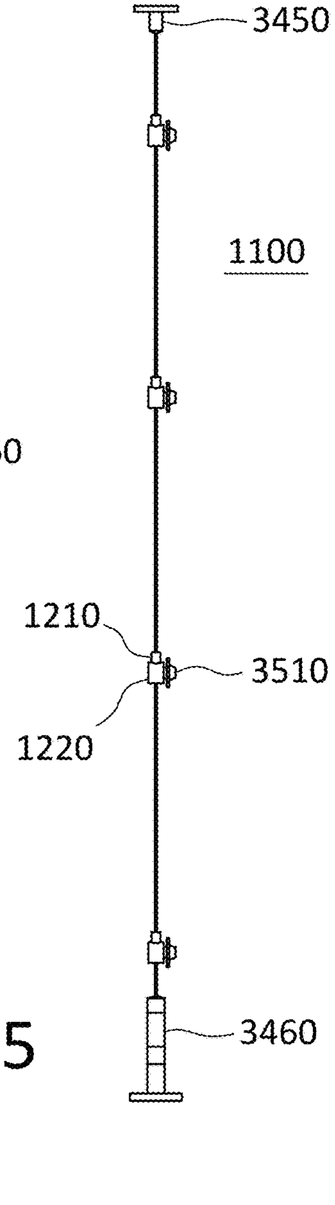
FIG. 35 is a side view of the cable rack apparatus of FIG. 34.

FIG. 35 is a side view of cable rack system 1100. This view shows one or more fasteners 3510, one or more cable grippers 1220, one or more cable gripper caps 1210, top anchor 3450, and bottom anchor 3460. Fastener 3510 can be configured to receive fastener 3420 (shown in FIG. 34). An LED board 3410 can be coupled between fastener 3510 and fastener 3420. Fastener 3510 can be similar or identical to fastener 303 as shown in FIG. 14.

The foregoing is provided for purposes of illustrating, explaining, and describing embodiments of these disclosures. Modifications and adaptations to these embodiments will be apparent to those skilled in the art and may be made without departing from the scope or spirit of these disclosures.

Although the cable rack systems have been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-35 may be modified, and that the foregoing discussion of certain of these embodiments does not necessarily represent a complete description of all possible embodiments. For example, one or more of the procedures, processes, or activities of FIGS. 32-33 may include different procedures, processes, and/or activities and be performed by many different modules, in many different orders, and/or one or more of the procedures, processes, or activities of FIGS. 32-33 may include one or more of the procedures, processes, or activities of another different one of FIGS. 32-33. As another example, the elements within cable rack system 100 (FIG. 1), cable rack system 200 (FIGS. 2-5), cable rack system 400 (FIG. 21), cable rack system 600 (FIG. 24), cable rack system 700 (FIGS. 25, 26, 28), cable rack system 800 (FIG. 29), cable rack system 3010 (FIG. 30), cable rack system 3110 (FIG. 31), and cable rack system 1100 (FIGS. 34-35) can be interchanged or otherwise modified.

Replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A cable rack system comprising:
comprising one or more sections of approximately 15.27 square inches of cross sectional area comprising:
one or more cables;
one or more clips coupled to the one or more cables and configured to receive one or more ultraviolet (“UV”) emitters;
two or more surface mounts configured to couple the one or more cables to one or more surfaces;
one or more bottom set screws each further comprising a slot to allow the excess cable from the one or more cables to be released from the side of the bottom set screw; and
one or more top set screws;
wherein the one or more bottom set screws and the one or more top set screws are coupled to the two or more surface mounts to facilitate creating tension along the one or more cables between the two or more surface mounts.

2. The cable rack system of claim 1, wherein a tensioning mechanism coupled to the one or more cables is operable to adjust tension in the one or more cables between the two or more surface mounts.

3. The cable rack system of claim 2, wherein the one or more cables extend from a portion of the tensioning mechanism to allow the one or more cables to be pulled by a user to create tension between the two or more surface mounts.

4. The cable rack system of claim 1, wherein at least one of the UV emitters is an LED board with one or more LED lights wherein the LED board is coupled to the one or more cables.

5. The cable rack system of claim 1, wherein a compression mechanism coupled to the one or more UV emitters allows a position of the one or more UV emitters to be adjusted to alter a distance between the one or more UV emitters and the two or more surface mounts.

6. The cable rack system of claim 1, wherein at least one of the two or more surface mounts is coupled to a track surface.

7. The cable rack system of claim 6, wherein at least one of the two or more surface mounts is adjustable to couple to different locations along the track surface.

8. The cable rack system of claim 1, wherein at least one of the two or more surface mounts is configured to couple the cable rack system to a floor or ceiling surface.

9. The cable rack system of claim 1, wherein at least one of the two or more surface mounts extends approximately perpendicular to the one or more cables to couple the cable rack system to one or more surfaces approximately parallel to the one or more cables.

10. The cable rack system of claim 1, wherein at least one of the two or more surface mounts is coupled to a sliding frame.

11. The cable rack system of claim 1, wherein the one or more cables are approximately parallel to the one or more UV emitters coupled to the one or more cables.

12. The cable rack system of claim 1, wherein the one or more cables are approximately perpendicular to the one or more UV emitters coupled to the one or more cables.

13. The cable rack system of claim 1, wherein the one or more UV emitters are configured to irradiate on one or more components of an air handling system.

14. The cable rack system of claim 1, wherein the one or more UV emitters are configured to irradiate on a vertically oriented object.

15. A method for providing a cable rack system comprising one or more sections of approximately 15.27 square inches of cross sectional area further comprising:

providing one or more cables;

providing one or more UV emitters;

providing one or more bottom set screws each further comprising a slot to allow the excess cable from the one or more cables to be released from the side of the bottom set screw;

providing one or more top set screws; and providing two or more surface mounts configured to couple the one or more cables to two or more surfaces;

wherein the one or more bottom set screws and the one or more top set screws are coupled to the two or more surface mounts to facilitate creating tension along the one or more cables between the two or more surface mounts.

16. The method of claim 15 further comprising: providing one or more clips coupling the one or more cables to the one or more UV emitters.

17. The method of claim 15 further comprising: providing a frame with one or more wheels to couple at least one of the one or more surface mounts to the frame to secure the cable rack system.

18. A method of installing a cable rack system comprising one or more sections of approximately 15.27 square inches of cross sectional area further comprising:

coupling one or more UV emitters to one or more cables using one or more clips; and coupling the one or more cables to two or more surfaces using two or more surface mounts;

coupling one or more bottom set screws each further comprising a slot to allow the excess cable from the one or more cables to be released from the side of the bottom set screw to at least one of the surface mounts; and coupling one or more top set screws to at least one of the surface mounts;

wherein the one or more bottom set screws and the one or more top set screws are coupled to the two or more surface mounts to facilitate creating tension along the one or more cables between the two or more surface mounts.

19. The method of claim 18 further comprising: coupling at least one of the two or more surface mounts to a frame with one or more wheels.

* * * * *